US011559662B2

(12) United States Patent
Hopkinson et al.

(10) Patent No.: US 11,559,662 B2
(45) Date of Patent: Jan. 24, 2023

(54) STEERABLE DRAINAGE DEVICES

(71) Applicant: Merit Medical Systems, Inc., South Jordan, UT (US)

(72) Inventors: Aaron Hopkinson, Herriman, UT (US); Alan Vawdrey, Riverton, UT (US); Jason Wiersdorf, West Jordan, UT (US); Richard Barlow, American Fork, UT (US); Jordan Peterson, West Jordan, UT (US); Tyler Rees, Draper, UT (US); Richard Stephenson, Salt Lake City, UT (US); Derek Jensen, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 543 days.

(21) Appl. No.: 16/382,530

(22) Filed: Apr. 12, 2019

(65) Prior Publication Data

US 2019/0314609 A1 Oct. 17, 2019

Related U.S. Application Data

(60) Provisional application No. 62/657,268, filed on Apr. 13, 2018.

(51) Int. Cl.
*A61M 25/01* (2006.01)
*A61M 27/00* (2006.01)
*A61M 25/00* (2006.01)

(52) U.S. Cl.
CPC .... *A61M 25/0136* (2013.01); *A61M 25/0147* (2013.01); *A61M 27/00* (2013.01); *A61M 25/007* (2013.01)

(58) Field of Classification Search
CPC .......... A61M 25/0136; A61M 25/0147; A61M 27/00; A61B 2017/2923; A61B 2018/00946; A61B 2017/00367; A61B 2017/00371; A61B 2017/0038;
(Continued)

(56) References Cited

U.S. PATENT DOCUMENTS

| 2,393,002 A | 1/1946 | Larkin |
| 2,898,917 A | 8/1959 | Wallace |
| 3,225,762 A | 12/1965 | Guttman |

(Continued)

FOREIGN PATENT DOCUMENTS

| RU | 2012371 | 5/1994 |
| RU | 2415682 | 4/2011 |

(Continued)

OTHER PUBLICATIONS

International Preliminary Report and Written Opinion dated Dec. 27, 2016 for PCT/US2015/038112.
(Continued)

*Primary Examiner* — Adam Marcetich
(74) *Attorney, Agent, or Firm* — Dorsey & Whitney LLP

(57) ABSTRACT

Steerable, elongated medical devices that are inserted into a patient's body are disclosed. The devices include first and second wires slidably extending longitudinally through a wall of a tube and attached adjacent a distal end of the tube. The devices also include a tension control member configured to selectively apply a tension force to the wires to bend the tube.

14 Claims, 28 Drawing Sheets

(58) Field of Classification Search
CPC ........... A61B 2017/00384; A61B 2017/00389;
A61B 2017/00407
See application file for complete search history.

(56) References Cited

U.S. PATENT DOCUMENTS

| | | | |
|---|---|---|---|
| 3,416,532 A | 12/1968 | Grossman | |
| 3,610,231 A | 10/1971 | Takahashi et al. | |
| 3,683,929 A | 8/1972 | Holter | |
| 3,830,238 A | 8/1974 | Kurtz et al. | |
| 3,863,641 A | 2/1975 | Popa | |
| 3,867,945 A | 2/1975 | Long | |
| 3,937,418 A | 2/1976 | Critelli | |
| 3,943,929 A | 3/1976 | Patel | |
| 4,068,383 A | 1/1978 | Krebs | |
| 4,105,031 A | 8/1978 | Kurtz et al. | |
| 4,202,510 A | 5/1980 | Stanish | |
| 4,203,430 A | 5/1980 | Takahashi | |
| 4,228,802 A | 10/1980 | Trott et al. | |
| 4,439,189 A | 3/1984 | Sargeant et al. | |
| 4,467,802 A * | 8/1984 | Maslanka | A61B 17/221 |
| | | | 294/100 |
| 4,571,239 A | 2/1986 | Heyman | |
| 4,580,551 A | 4/1986 | Siegmund et al. | |
| 4,608,982 A | 9/1986 | Pollard | |
| 4,692,154 A | 9/1987 | Singery et al. | |
| 4,769,019 A | 9/1988 | Kerwin | |
| 4,846,171 A * | 7/1989 | Kauphusman | A61B 18/245 |
| | | | 219/121.61 |
| 4,862,891 A | 9/1989 | Smith | |
| 4,883,474 A | 11/1989 | Sheridan et al. | |
| 4,920,980 A | 5/1990 | Jackowski | |
| 5,026,358 A | 6/1991 | Everett et al. | |
| 5,040,543 A | 8/1991 | Badera | |
| 5,047,018 A | 9/1991 | Gay | |
| 5,084,054 A * | 1/1992 | Bencini | A61B 17/2909 |
| | | | 606/113 |
| 5,108,368 A | 4/1992 | Hammerslag et al. | |
| 5,141,503 A | 8/1992 | Sewell | |
| 5,157,813 A | 10/1992 | Carroll | |
| 5,205,830 A | 4/1993 | Dassa et al. | |
| 5,207,661 A | 5/1993 | Repschlager | |
| 5,211,644 A | 5/1993 | Vanbeek et al. | |
| 5,297,310 A | 3/1994 | Cox et al. | |
| 5,300,050 A | 4/1994 | Everett et al. | |
| 5,312,357 A | 5/1994 | Buijs | |
| 5,364,351 A | 11/1994 | Heinzelman et al. | |
| 5,370,610 A | 12/1994 | Reynolds et al. | |
| 5,397,321 A | 3/1995 | Houser et al. | |
| 5,409,462 A | 4/1995 | Ross | |
| 5,409,468 A | 4/1995 | Sachse | |
| 5,441,483 A * | 8/1995 | Avitall | A61B 18/1492 |
| | | | 604/95.05 |
| 5,456,664 A | 10/1995 | Heinzelman et al. | |
| 5,492,535 A * | 2/1996 | Reed | F04B 9/14 |
| | | | 604/152 |
| 5,522,833 A * | 6/1996 | Stephens | A61B 17/3496 |
| | | | 606/185 |
| 5,540,648 A | 7/1996 | Yoon et al. | |
| 5,601,087 A | 2/1997 | Gunderson et al. | |
| 5,616,131 A | 4/1997 | Sauer | |
| 5,630,795 A | 5/1997 | Kuramoto et al. | |
| 5,653,696 A | 8/1997 | Shiber et al. | |
| 5,772,670 A | 6/1998 | Brosa | |
| 5,807,341 A | 9/1998 | Heim et al. | |
| 5,895,400 A | 4/1999 | Abela | |
| 5,897,534 A | 4/1999 | Heim et al. | |
| 5,904,667 A | 5/1999 | Falwell | |
| 5,944,690 A | 8/1999 | Falwell et al. | |
| 5,987,344 A | 11/1999 | West | |
| 6,003,736 A * | 12/1999 | Ljunggren | A61M 5/20 |
| | | | 222/386 |
| 6,045,623 A | 4/2000 | Cannon et al. | |
| 6,086,600 A * | 7/2000 | Kortenbach | A61B 17/10 |
| | | | 606/220 |
| 6,146,355 A | 11/2000 | Biggs | |
| 6,171,277 B1 | 1/2001 | Ponzi | |
| 6,183,450 B1 | 2/2001 | Lois | |
| 6,193,691 B1 | 2/2001 | Beardsley | |
| 6,254,581 B1 | 7/2001 | Scott | |
| 6,468,260 B1 | 10/2002 | Bumbalough et al. | |
| 6,500,167 B1 | 12/2002 | Webster | |
| 6,514,273 B1 | 2/2003 | Voss et al. | |
| 6,530,913 B1 | 3/2003 | Giba et al. | |
| 6,530,935 B2 | 3/2003 | Wensel et al. | |
| 6,638,253 B2 | 10/2003 | Breznock | |
| 6,907,992 B2 | 6/2005 | McMichael et al. | |
| 7,037,290 B2 | 5/2006 | Gardeski et al. | |
| 7,407,128 B1 | 8/2008 | Chang | |
| 7,497,854 B2 | 3/2009 | Gill et al. | |
| 7,578,814 B2 | 8/2009 | Accisano et al. | |
| 7,740,623 B2 | 6/2010 | Nayak et al. | |
| 7,758,586 B2 | 7/2010 | Muto et al. | |
| 8,220,460 B2 | 7/2012 | Tanaka | |
| 8,246,752 B2 | 8/2012 | Boyle, Jr. | |
| D669,168 S | 10/2012 | Krueger et al. | |
| D669,577 S | 10/2012 | Holsinger | |
| 8,388,759 B2 | 3/2013 | Boyle, Jr. et al. | |
| 8,409,070 B2 | 4/2013 | Carol et al. | |
| D700,322 S | 2/2014 | Kleiner | |
| D708,741 S | 7/2014 | Harrison et al. | |
| D710,495 S | 8/2014 | Wu et al. | |
| 8,870,892 B2 | 10/2014 | Feng et al. | |
| D718,440 S | 11/2014 | Besse et al. | |
| D724,725 S | 3/2015 | Chang | |
| 8,979,744 B2 | 3/2015 | Braga et al. | |
| D726,304 S | 4/2015 | Yatabe et al. | |
| D728,781 S | 5/2015 | Pierson et al. | |
| D732,160 S | 6/2015 | Du | |
| 9,604,033 B2 | 3/2017 | Lazarus | |
| 9,649,415 B2 | 5/2017 | Lazarus | |
| 9,821,097 B2 | 11/2017 | Lazarus | |
| 10,232,150 B2 * | 3/2019 | Lazarus | A61M 1/84 |
| 2001/0005785 A1 | 6/2001 | Sachse | |
| 2001/0007922 A1 | 7/2001 | Schwager | |
| 2002/0082617 A1 * | 6/2002 | Nishtala | A61B 17/3478 |
| | | | 606/139 |
| 2003/0208252 A1 | 11/2003 | O'Boyle et al. | |
| 2003/0225364 A1 | 12/2003 | Kraft et al. | |
| 2003/0236493 A1 | 12/2003 | Mauch | |
| 2004/0035017 A1 | 2/2004 | Yang | |
| 2004/0059293 A1 | 3/2004 | Chu et al. | |
| 2004/0116852 A1 | 6/2004 | Scopton | |
| 2004/0143197 A1 | 7/2004 | Soukup et al. | |
| 2005/0119655 A1 * | 6/2005 | Moses | A61B 18/1442 |
| | | | 606/171 |
| 2005/0131393 A1 | 6/2005 | Chu | |
| 2005/0184186 A1 | 8/2005 | Tsoi et al. | |
| 2005/0222568 A1 * | 10/2005 | O'Sullivan | A61B 18/14 |
| | | | 606/47 |
| 2005/0277875 A1 | 12/2005 | Selkee | |
| 2006/0052811 A1 * | 3/2006 | Blanco | A61B 17/3496 |
| | | | 606/185 |
| 2006/0069311 A1 | 3/2006 | Sullivan | |
| 2006/0074417 A1 * | 4/2006 | Cunningham | A61B 18/1442 |
| | | | 606/51 |
| 2006/0142695 A1 | 6/2006 | Knudson | |
| 2006/0167452 A1 * | 7/2006 | Moses | A61B 18/1442 |
| | | | 606/171 |
| 2006/0173449 A1 | 8/2006 | Sharareh et al. | |
| 2006/0217667 A1 | 9/2006 | Accisano et al. | |
| 2006/0253140 A1 * | 11/2006 | Ortiz | A61B 17/1114 |
| | | | 606/153 |
| 2006/0264925 A1 | 11/2006 | Sharareh et al. | |
| 2006/0264988 A1 | 11/2006 | Boyle | |
| 2006/0280773 A1 | 12/2006 | Roschak et al. | |
| 2007/0016133 A1 | 1/2007 | Pepper | |
| 2007/0060997 A1 | 3/2007 | De Boer | |
| 2007/0078455 A1 | 4/2007 | Rashidi | |
| 2007/0156116 A1 | 7/2007 | Gonzalez | |
| 2007/0156225 A1 * | 7/2007 | George | A61M 25/0136 |
| | | | 623/1.12 |
| 2007/0167923 A1 | 7/2007 | Deal | |

(56) References Cited

U.S. PATENT DOCUMENTS

| | | |
|---|---|---|
| 2007/0287993 A1 | 12/2007 | Hinman et al. |
| 2008/0021415 A1 | 1/2008 | Durkin et al. |
| 2008/0236209 A1 | 1/2008 | Conti |
| 2008/0045921 A1 | 2/2008 | Anderson et al. |
| 2008/0097293 A1 | 4/2008 | Chin |
| 2008/0125848 A1 | 5/2008 | Kusleika et al. |
| 2008/0214948 A1 | 9/2008 | Myklebust et al. |
| 2008/0300462 A1 | 12/2008 | Intoccia et al. |
| 2009/0005771 A1 | 1/2009 | Lieber et al. |
| 2009/0012365 A1 | 1/2009 | Ueno et al. |
| 2009/0050146 A1* | 2/2009 | Smith ............... A61M 16/0488 |
| | | 128/200.26 |
| 2009/0062769 A1 | 3/2009 | Graves |
| 2009/0187168 A1* | 7/2009 | Maeda ............... A61M 25/0113 |
| | | 606/1 |
| 2009/0227900 A1 | 9/2009 | Kim |
| 2009/0270800 A1 | 10/2009 | Spurchise et al. |
| 2009/0270838 A1 | 10/2009 | Berthiaume |
| 2009/0299327 A1 | 12/2009 | Tilson et al. |
| 2010/0069834 A1 | 3/2010 | Schultz |
| 2010/0070024 A1 | 3/2010 | Venturelli et al. |
| 2010/0101061 A1 | 4/2010 | Ha |
| 2010/0137775 A1 | 6/2010 | Hu et al. |
| 2010/0145368 A1 | 6/2010 | Chu et al. |
| 2010/0168731 A1 | 7/2010 | Wu et al. |
| 2010/0191057 A1 | 7/2010 | Jansen et al. |
| 2010/0222664 A1 | 9/2010 | Lemon |
| 2010/0234799 A1 | 9/2010 | Paris et al. |
| 2010/0249490 A1 | 9/2010 | Farnan |
| 2010/0249520 A1 | 9/2010 | Shelton, IV et al. |
| 2010/0264244 A1 | 10/2010 | Spencer |
| 2011/0040285 A1 | 2/2011 | Boyle |
| 2011/0062268 A1 | 3/2011 | Cheng |
| 2011/0077498 A1 | 3/2011 | McDaniel |
| 2011/0197888 A1 | 8/2011 | Deutsch et al. |
| 2011/0213300 A1 | 9/2011 | McWeeney et al. |
| 2011/0224647 A1 | 9/2011 | Lazarus |
| 2011/0264089 A1 | 10/2011 | Zirkle et al. |
| 2011/0282153 A1 | 11/2011 | Ueki |
| 2012/0116161 A1 | 5/2012 | Ueki |
| 2012/0157921 A1 | 6/2012 | Hoofnagle |
| 2012/0172703 A1 | 7/2012 | Esguerra et al. |
| 2013/0023840 A1 | 1/2013 | Loske et al. |
| 2013/0046250 A1 | 2/2013 | Bode |
| 2013/0090529 A1 | 4/2013 | Boulais |
| 2013/0123803 A1 | 5/2013 | Kirschenman et al. |
| 2013/0158379 A1 | 6/2013 | Selkee |
| 2013/0184642 A1 | 7/2013 | O'Donnell et al. |
| 2013/0204087 A1 | 8/2013 | Jaworek et al. |
| 2013/0211385 A1 | 8/2013 | Lazarus |
| 2013/0253505 A1 | 9/2013 | Schultz |
| 2013/0276718 A1 | 10/2013 | Valadez et al. |
| 2013/0310767 A1 | 11/2013 | Solar |
| 2014/0088496 A1 | 3/2014 | Tegg |
| 2014/0114403 A1* | 4/2014 | Dale .................... A61B 17/068 |
| | | 623/2.11 |
| 2014/0150782 A1 | 6/2014 | Vazales et al. |
| 2014/0193138 A1 | 7/2014 | Koren |
| 2014/0290014 A1 | 10/2014 | Myrick |
| 2015/0148595 A1 | 5/2015 | Bagwell et al. |
| 2015/0157399 A1 | 6/2015 | Romoscanu |
| 2015/0335861 A1 | 11/2015 | Osypka |
| 2015/0374889 A1 | 12/2015 | Lazarus |
| 2015/0374959 A1 | 12/2015 | Lazarus |
| 2017/0050041 A1 | 2/2017 | Cosman |
| 2017/0143940 A1 | 5/2017 | Flygare et al. |
| 2017/0156711 A1* | 6/2017 | Jogasaki .......... A61B 17/00234 |
| 2017/0224955 A1* | 8/2017 | Douglas ............. A61M 25/0113 |
| 2017/0354206 A1 | 12/2017 | Hammerslag et al. |
| 2018/0263682 A1* | 9/2018 | Mills ................. A61B 18/1492 |
| 2019/0374214 A1* | 12/2019 | Bohl ..................... A61B 90/50 |

FOREIGN PATENT DOCUMENTS

| | | |
|---|---|---|
| WO | 199325264 | 12/1993 |
| WO | 199952481 | 10/1999 |
| WO | 2017149416 | 9/2017 |

OTHER PUBLICATIONS

International Search Report and Written Opinion dated Mar. 8, 2017 for PCT/US2016/063251.

International Search Report and Written Opinion dated Aug. 6, 2019 for PCT/US2019/027193.

International Search Report and Written Opinion dated Aug. 27, 2015 for PCT/US2015/038086.

International Search Report and Written Opinion dated Oct. 1, 2015 for PCT/US2015/038112.

International Search Report dated Sep. 3, 2015 for PCT/US2015/038102.

Notice of Allowance dated Feb. 28, 2019 for U.S. Appl. No. 15/358,549.

Notice of Allowance dated Oct. 16, 2018 for U.S. Appl. No. 13/840,986.

Office Action dated May 11, 2017 for U.S. Appl. No. 14/318,571.

Office Action dated Jun. 14, 2018 for U.S. Appl. No. 13/840,986.

Office Action dated Sep. 12, 2017 for U.S. Appl. No. 14/318,571.

Office Action dated Oct. 30, 2018 for U.S. Appl. No. 15/358,549.

Office Action dated Nov. 3, 2017 for U.S. Appl. No. 13/840,986.

Office Action dated Dec. 7, 2012 for U.S. Appl. No. 13/045,274.

Catheter Prevents Clogging, Research & Development <http://www.rdmag.com-printpdf/award-winners/2011/08/catheter-prevents-clogging> ,Aug. 14, 2011 ,3 pages.

Express Dry Seal Chest Drain, Instructions for Use, Atruim www.atriummed.com ,2003 ,2 pgs.

Medical Plueroscopy, Cancer Treatment Centers of America , retrieved Aug. 19, 2013 <hhtp7/www.cancercenter.com/treatments/medical-pleuroscopy/> ,Aug. 19, 2013 ,2 pages.

Occlutech Steerable Guiding Sheath, ,2015.

Rocket® Cardiothoracic Range, Rocketmedical, Issue 1, R89947 ,Jan. 2011 ,23 pages.

Ben-Isaac, et al.,Flexible Fiberoptic Pleuroscopy: Pleural and Lung Biopsy, Experimental Approaches, Chest Journal No. 67, <http://www.rdmag.com/printpdf/award-winners-2011/08/catheter-prevents-clogging> ,May 5, 1975 ,573-576.

Notice of Allowance dated Jan. 5, 2017 for U.S. Appl. No. 14/318,571.

Notice of Allowance dated Feb. 6, 2018 for U.S. Appl. No. 14/318,571.

Notice of Allowance dated May 9, 2018 for U.S. Appl. No. 14/318,571.

Notice of Allowance dated Sep. 20, 2017 for U.S. Appl. No. 14/318,568.

Notice of Allowance dated Nov. 9, 2016 for U.S. Appl. No. 14/318,550.

Office Action dated Jan. 21, 2016 for U.S. Appl. No. 13/840,986.

Office Action dated Apr. 25, 2017 for U.S. Appl. No. 14/318,568.

Office Action dated Jul. 21, 2016 for U.S. Appl. No. 14/318,550.

Office Action dated Aug. 10, 2016 for U.S. Appl. No. 14/318,560.

Office Action dated Aug. 10, 2016 for U.S. Appl. No. 14/318,568.

Office Action dated Aug. 10, 2016 for U.S. Appl. No. 14/318,571.

Office Action dated Aug. 14, 2015 for U.S. Appl. No. 13/840,986.

Office Action dated Dec. 12, 2016 for U.S. Appl. No. 14/318,568.

Office Action dated Dec. 15, 2016 for U.S. Appl. No. 13/840,986.

* cited by examiner

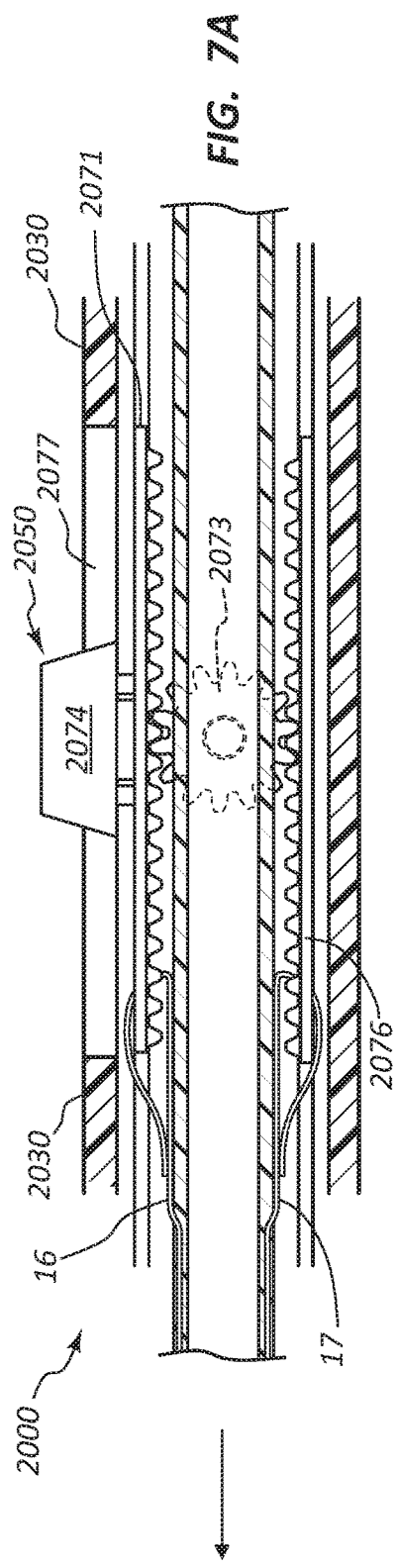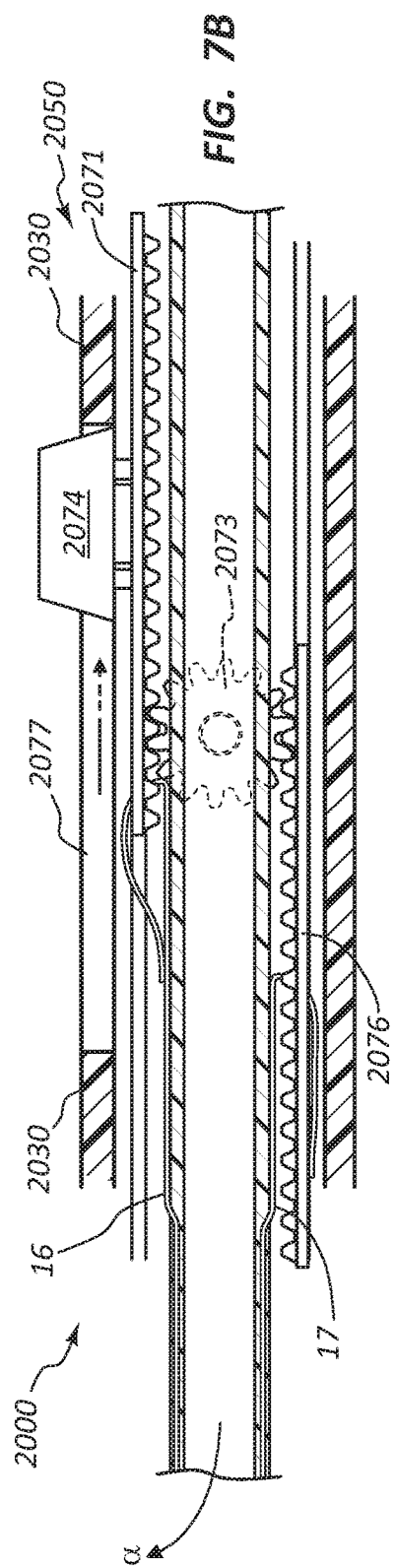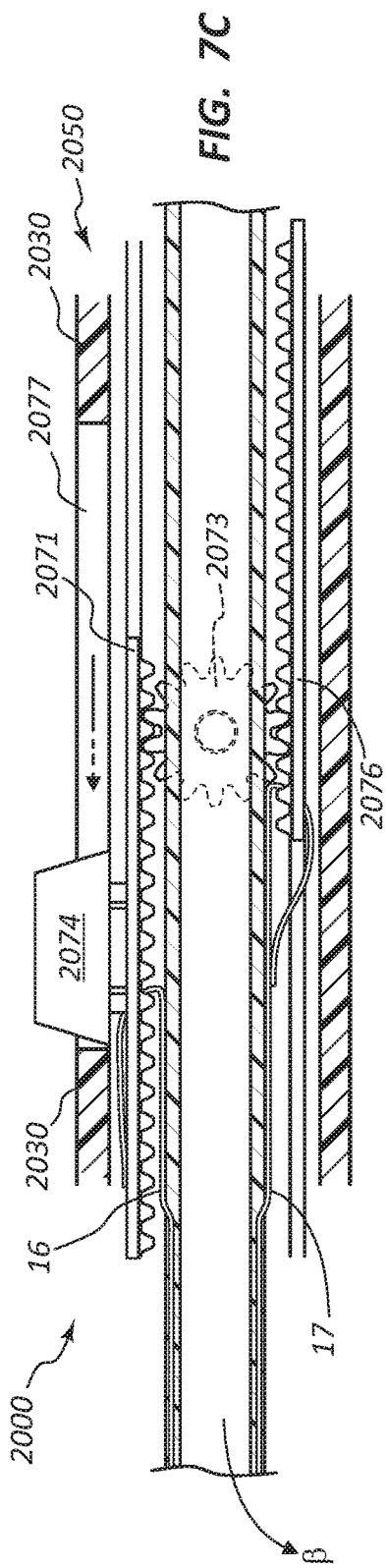

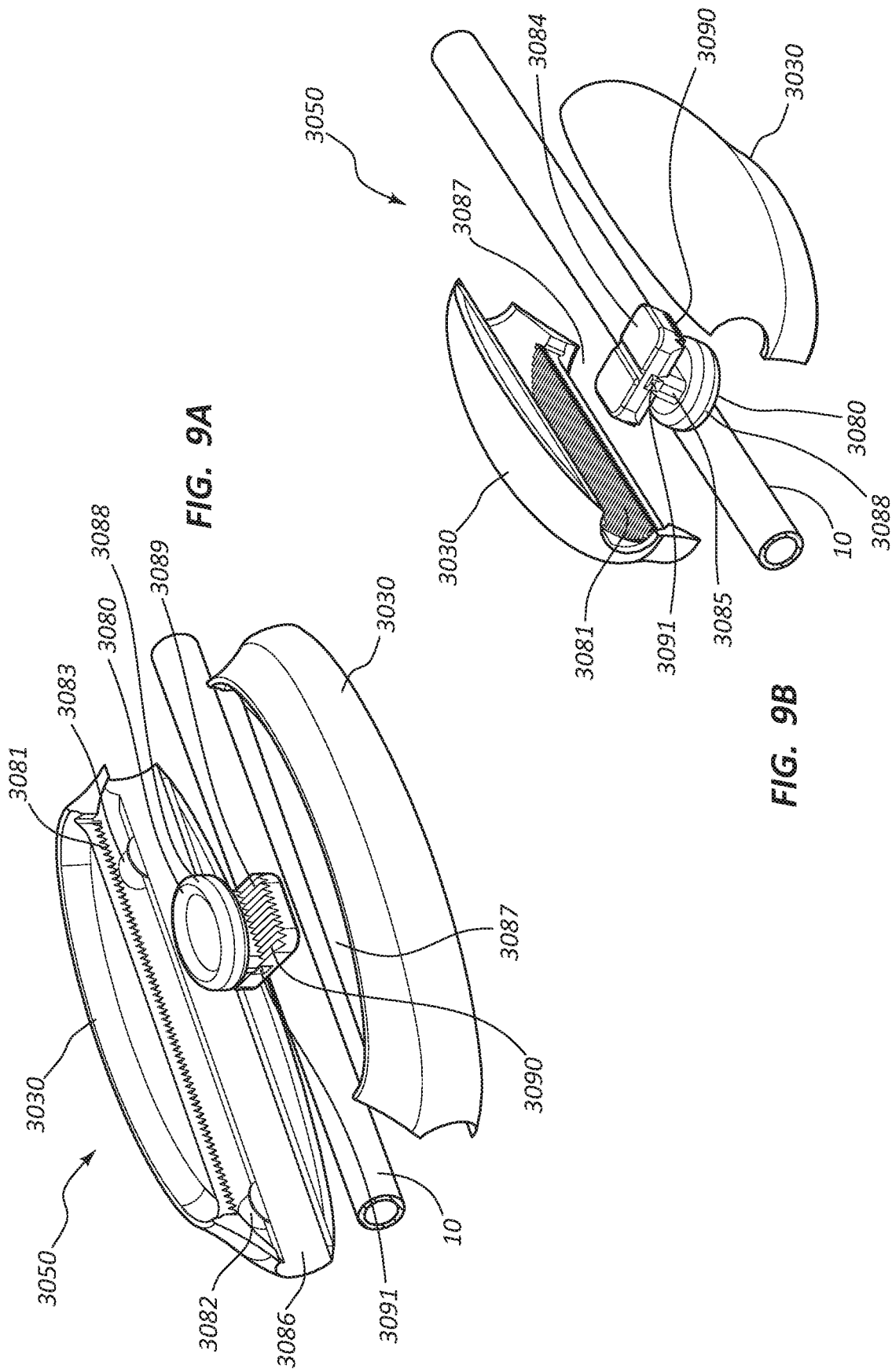

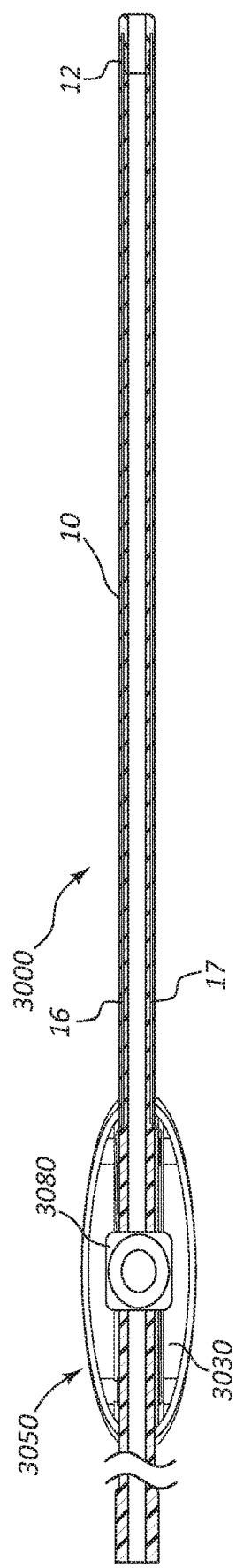
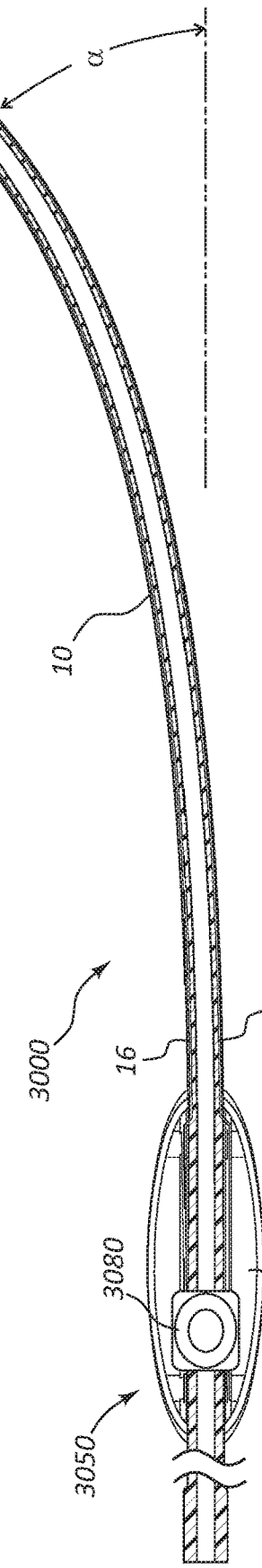
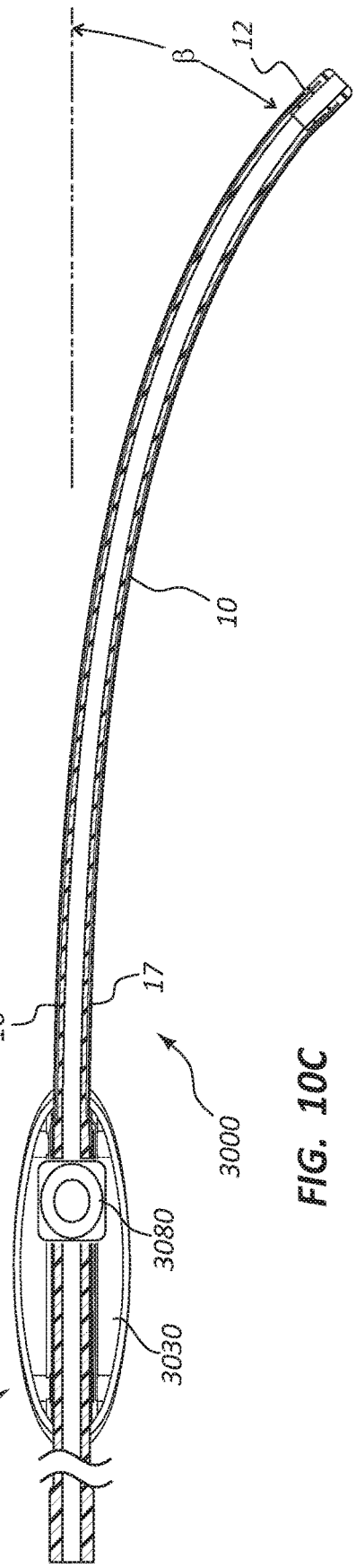
FIG. 10A
FIG. 10B
FIG. 10C

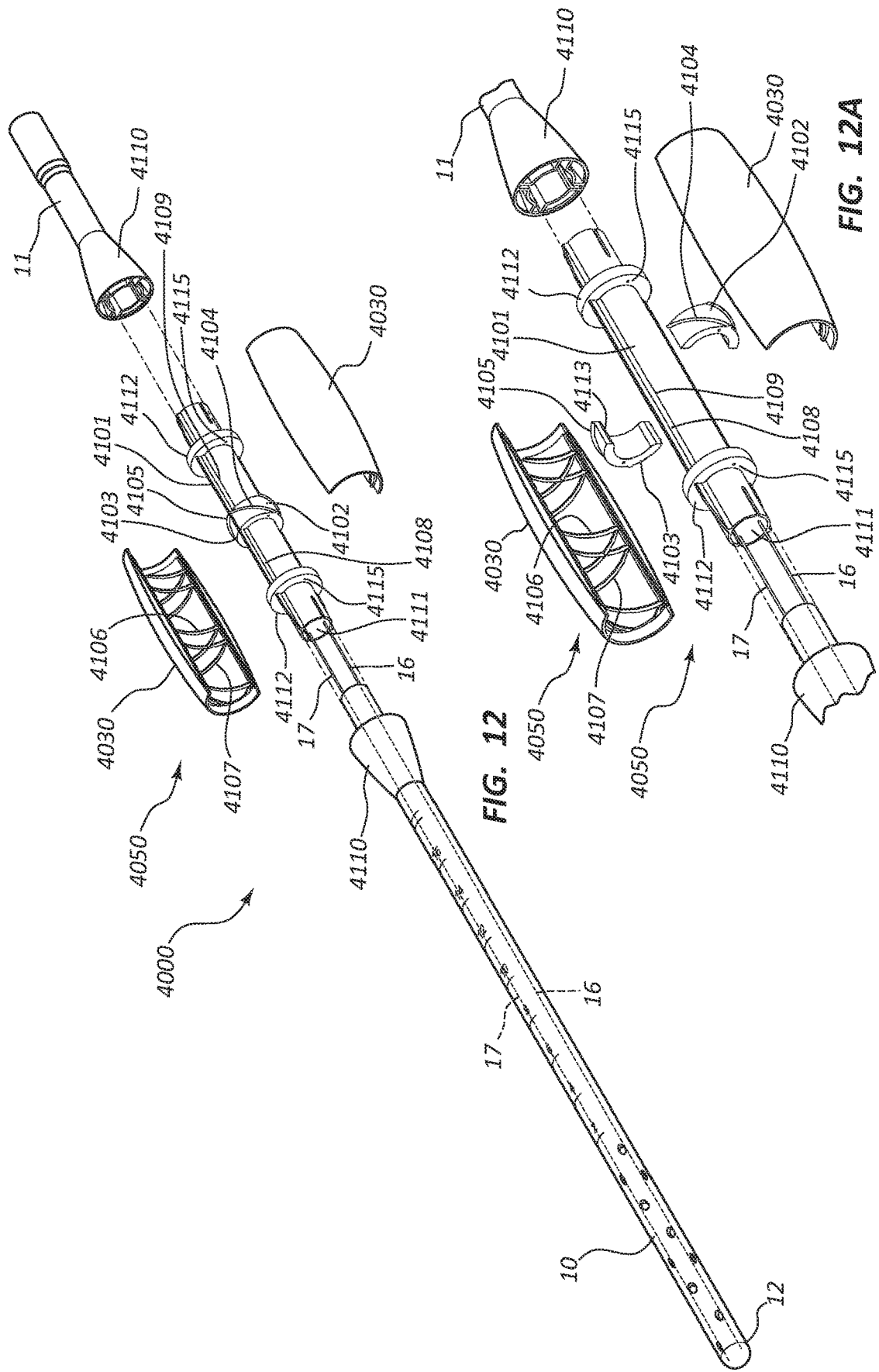

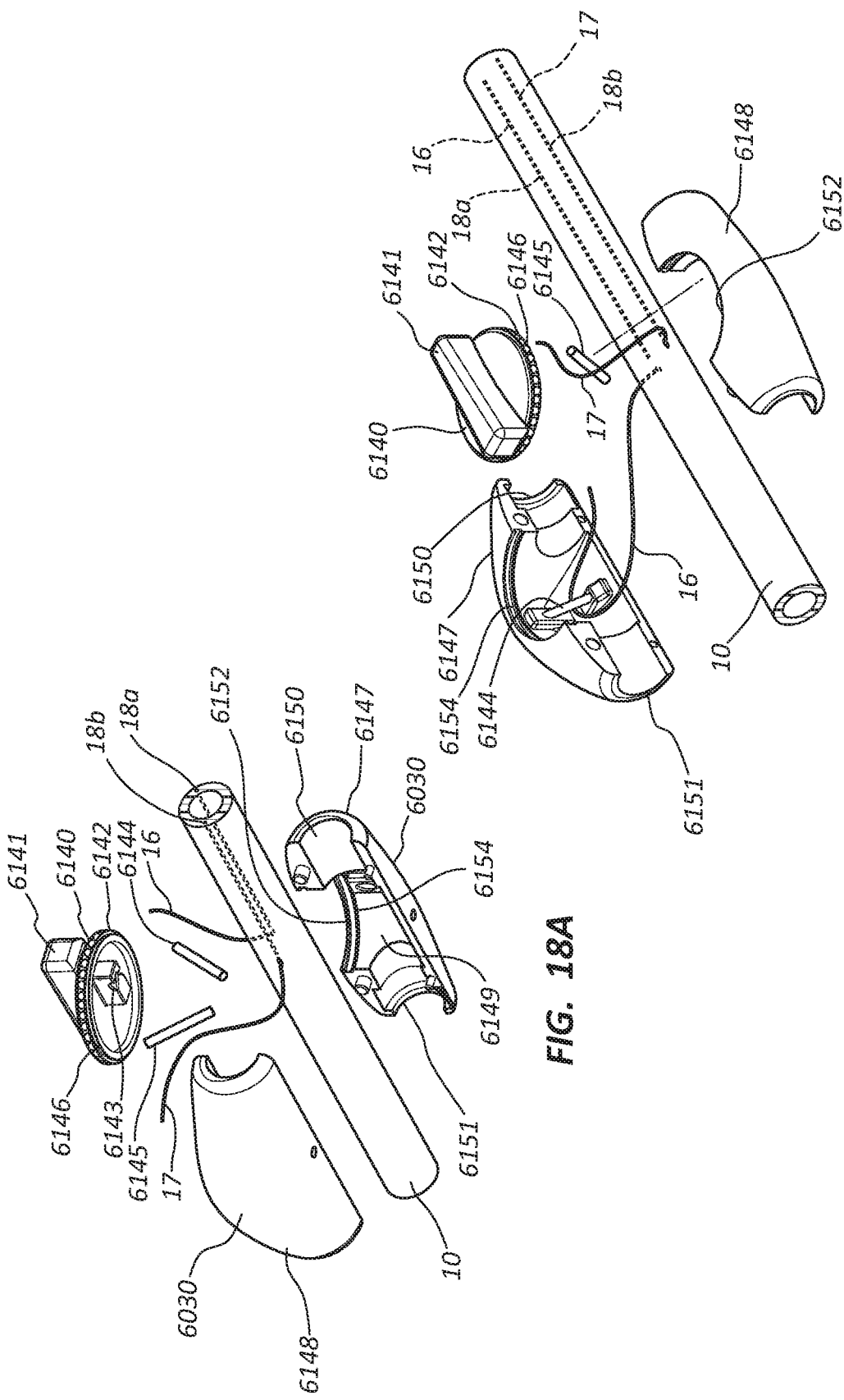

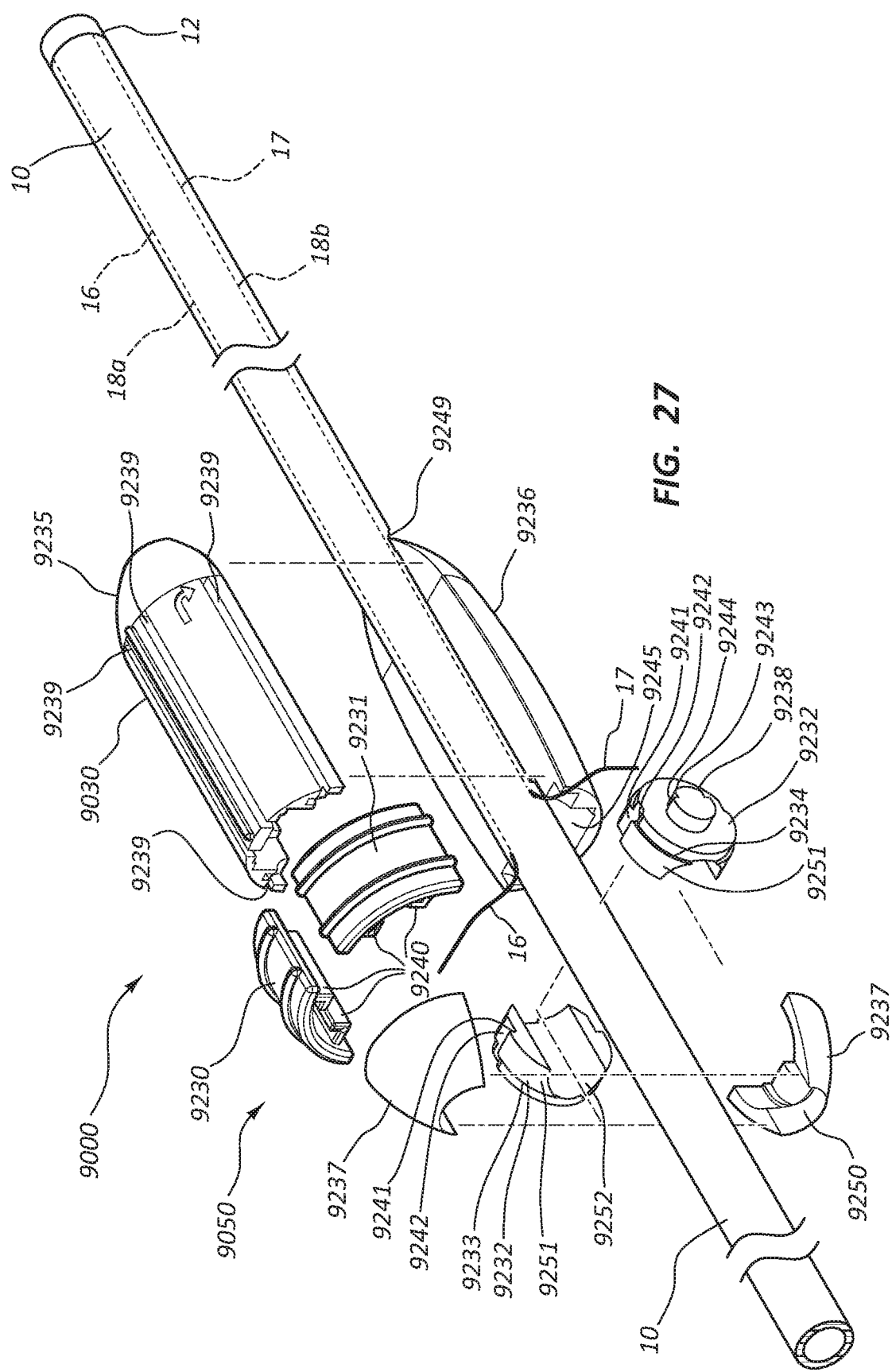

STEERABLE DRAINAGE DEVICES

RELATED APPLICATIONS

This application claims priority to U.S. Provisional Application No. 62/657,268, filed on Apr. 13, 2018 and titled, "Steerable Drainage Devices," which is hereby incorporated by reference in its entirety.

TECHNICAL FIELD

The present disclosure relates generally to elongated medical devices configured for insertion into a cavity or vessel of a patient. More specifically, the present disclosure relates to steerable drainage devices used to steer a distal end of the elongated medical device to a targeted location within the patient.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 7A is a top cross-sectional/cut-away view of the steerable drainage device of FIG. 5 in a straight configuration.

FIG. 7B is a top cross-sectional/cut-away view of the steerable drainage device of FIG. 5, where the device is bent in a first direction.

FIG. 7C is a top cross-sectional/cut-away view of the steerable drainage device of FIG. 5, where the device is bent in a second direction.

FIG. 9A is a perspective, exploded, top view of a portion of the steerable drainage device of FIG. 8.

FIG. 9B is a perspective, exploded, bottom view of a portion of the steerable drainage device of FIG. 8.

FIG. 10A is a partial cross-sectional top view of the steerable drainage device of FIG. 8 in a straight configuration.

FIG. 10B is a partial cross-sectional top view of the steerable drainage device of FIG. 8, where the device is bent in a first direction.

FIG. 10C is a partial cross-sectional top view of the steerable drainage device of FIG. 8, where the device is bent in a second direction.

FIG. 12 is a perspective, exploded, view of the steerable drainage device of FIG. 11.

FIG. 12A is a perspective, exploded view of a tension control member of the steerable drainage device of FIG. 11.

FIG. 18A is a perspective, exploded, bottom view of a portion of the steerable drainage device of FIG. 17.

FIG. 18B is a perspective, exploded, top view of a portion of the steerable drainage device of FIG. 17.

FIG. 27 is a perspective, exploded, view of the steerable drainage device of FIG. 26.

DETAILED DESCRIPTION

Figure 1:
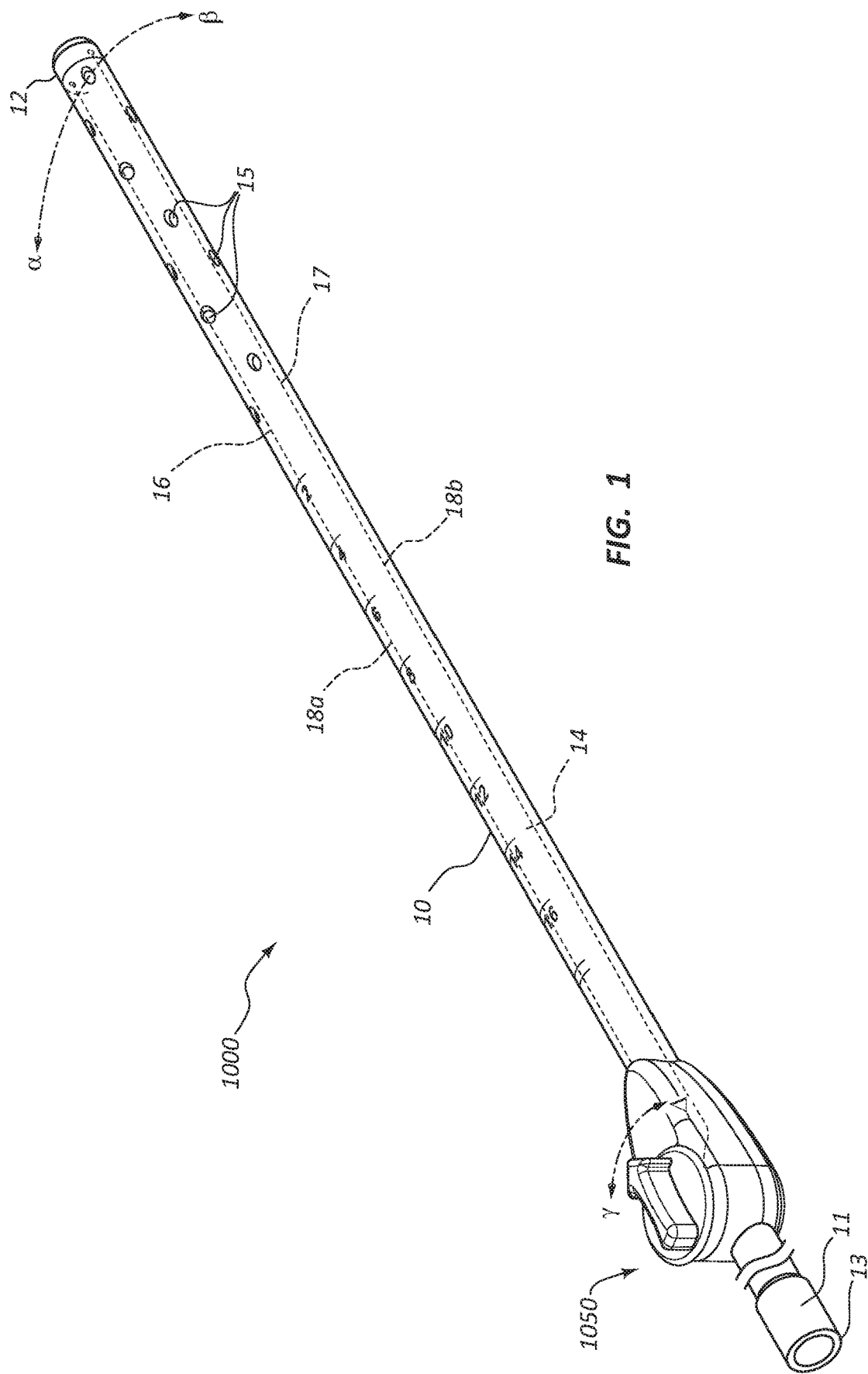
FIG. 1 is a perspective view of a steerable drainage device.

Elongate medical devices may be inserted into body cavities and vessels to perform diagnostic and therapeutic procedures. In some instances, positioning of the elongate device may be facilitated by a steering mechanism configured to bend or rotate an end of the elongate device such that the elongate device can be directed to, and positioned at, a targeted location. Examples of steerable elongated devices comprise balloon dilation catheters, stent delivery catheters, endoscopes, and drainage tubes, such as chest tubes. A chest tube, for example, may be steered to a targeted location within the pleural space to drain the space of excess fluid.

In some embodiments, the steerable drainage devices disclosed herein comprise two wires or flexible members running parallel over the length of a catheter or tube. The distal ends of the wires may be attached to a distal end of the catheter or tube. The proximal ends of the wires may be operatively coupled to a tension control member or steering device. As detailed below, in some embodiments, the tension control member is configured to selectively apply tension to the wires such that the end of the catheter or tube bends.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In the following disclosure various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to a drainage tube, the proximal end of the drainage tube refers to the end disposed outside of the patient and the distal end refers to the opposite end, the end disposed inside the patient.

"Fluid" is used in its broadest sense, to refer to any fluid, including both liquids and gases as well as solutions, compounds, suspensions, etc., which generally behave as fluids.

The terms "wire" or "flexible member" are broad terms that encompasses any type of flexible elongated material capable of providing a pulling force and encompasses, by way of example and not limitation, metal wire, coated wire, polymer wire, woven or braided wire, string, yarn, line, cable, filament, lace, and cord.

FIGS. 1-28C illustrate different views of several embodiments of steerable drainage devices and related components. These drainage devices and steering systems may be used in connection with a variety of drainage devices, including, for example, a chest tube. The steerable drainage devices disclosed herein are not limited to use with chest tubes, but may be used with any suitable elongate medical device, such as balloon dilatation catheters, stent delivery catheters, endoscopes, drainage tubes, etc., including devices configured to be directed to a target location. In certain views each device may be coupled to, or shown with, additional components not included in every view. Further, in some views only selected components are illustrated, to provide detail into the relationship of certain components. Some components may be shown in multiple views, but not discussed in connection with every view. Disclosure provided in connection with any figure or figure is relevant and may be analogously applied to disclosure provided in connection with any other figure or embodiment.

FIGS. 1-4C depict a steerable drainage device 1000. In the illustrated embodiment, the steerable drainage device 1000 comprises a drainage tube 10 and a tension control member or steering device 1050. The drainage tube 10 may comprise a proximal end 11, a distal end 12, a wall 13, a central lumen 14, and at least one closed lumens 18a, 18b. In some embodiments, the drainage tube 10 may comprise a single central lumen 14 forming a central passage through the drainage tube 10 and two closed lumens 18 disposed in the wall 13 of the drainage tube 10. The drainage tube 10 may be formed of a flexible polymer material, such as polyvinyl chloride (PVC), polyurethane; silicone, etc. . . . . . The drainage tube may further comprise a plurality of openings 15 near the distal end 12. The proximal end 11 of the drainage tube 10 may be configured for attachment to a vacuum source.

The distal end 12 of the drainage tube 10 may be configured to be detectable by an imaging system, such as x-ray, fluoroscopy, ultrasound, etc. The distal end 12 may comprise materials that are radiopaque, such as barium sulfate, bismuth trioxide, titanium bands, etc. In other embodiments, the distal end 12 may comprise materials or surface modifications that are configured to reflect ultrasound waves.

In certain embodiments, a first wire or flexible member 16 and a second wire or flexible member 17 may be inserted into the closed lumens 18a, 18b that are separate from the central lumen 14 of the drainage tube 10. The first and second wires 16, 17 may be attached to the distal end 12 of the drainage tube 10. As shown in FIG. 1, the closed lumens 18a, 18b and wires 16, 17 may be positioned on opposing sides of the drainage tube 10.

Coupling of the wires 16, 17 to the drainage tube 10 at or near the distal end 12 may be accomplished by one of any number of attachment configurations. In some embodiments, each wire 16, 17 may be wrapped around a portion of the distal end 12 of the drainage tube 10. Each wire 16, 17 may then be attached to itself at a joint, such as by a weld joint, a swaged or crimped joint, a knot, or another joint. In other embodiments, the drainage tube 10 may further comprise a tip comprising passages sized similar to the diameters of the wires 16, 17. The first wire 16 and the second wire 17 may extend through the passages of the tip, and a stop, such as a weld bead or a swaged member, may be attached to a free end of each wire 16, 17 to prevent the free end of each wire 16, 17 from passing through the passages. In yet further embodiments, a single wire may be utilized as the first wire 16 and the second wire 17 such that the single wire loops from a first proximal end to the distal end 12 of the drainage tube 10 and back to a second proximal end.

In operation, the distal end 12 of the drainage tube 10 may be displaced by manipulation of the wires 16, 17 at the proximal end 11 of the drainage tube 10. For example, when a tensile force is applied to the first wire 16 (e.g., when a pulling force is applied to the first wire 16 by a tension control member, such as tension control member 1050) a first side of the drainage tube 10 may be put into compression. When the first side of the drainage tube 10 is put into compression, the drainage tube 10 may bend in a first direction $\alpha$. Similarly, when a tensile force is applied to the second wire 17 (e.g., when a pulling force is applied to the second wire 17, such as by the tension control member 1050) a second side of the drainage tube 10 may be put into compression. When the second side of the drainage tube 10 is put into compression the drainage tube may bend in a second direction $\beta$.

Although the embodiment shown in FIG. 1 include a first wire and a second wire, different numbers of wires may be utilized. For example, a drainage tube may include only a first wire and not include a second wire. Additionally, a drainage tube may include a first wire, a second wire, and any number of additional wires. Generally, the more wires that are included, the greater the range of motion that may be achieved with a distal end of a drainage tube. For certain applications, two opposing wires configured to provide displacement in two directions may provide sufficient range of motion for many therapeutic uses, such as for draining fluid from the body cavity, for example, a pleural cavity.

As shown in FIGS. 1-4C, the steerable drainage device 1000 may comprise a tension control member 1050. The tension control member 1050 may be configured to apply selective tension to the wires 16, 17 such that the distal end 12 of the drainage tube 10 bends in a direction of a side of the drainage tube 10 where the tensioned wire 16, 17 is located, as described above. The tension control member 1050 may comprise a housing 1030, a knob 1056, a drive capstan 1053, a first spool 1054, a second spool 1055, and a locking member 1051.

The tension control member 1050 may be coupled to the drainage tube 10 adjacent the proximal end 11. In some embodiments, the tension control member 1050 may be fixedly coupled to the drainage tube 10 such that the tension control member 1050 is anchored to the drainage tube 10 to allow for application of tension to the wires 16, 17. A ring (not shown) may be fixedly coupled to the drainage tube 10 adjacent the proximal end 11 and the housing 1030 disposed over the ring such that the tension control member 1050 is prevented from longitudinal displacement relative to the drainage tube 10. Each embodiment of the steerable drainage device disclosed herein may be configured in a similar manner. The drainage tube 10 may be axially aligned with a longitudinal axis of the tension control member 1050 such that the drainage tube 10 passes through at least a portion of the housing 1030. The housing 1030 may be configured to be gripped by a hand of the healthcare worker. The housing 1030 may be sized to be comfortably secured to a patient's body for time periods hours to days. The tension control member 1050 may be at least partially disposed within the housing 1030.

Figure 2:
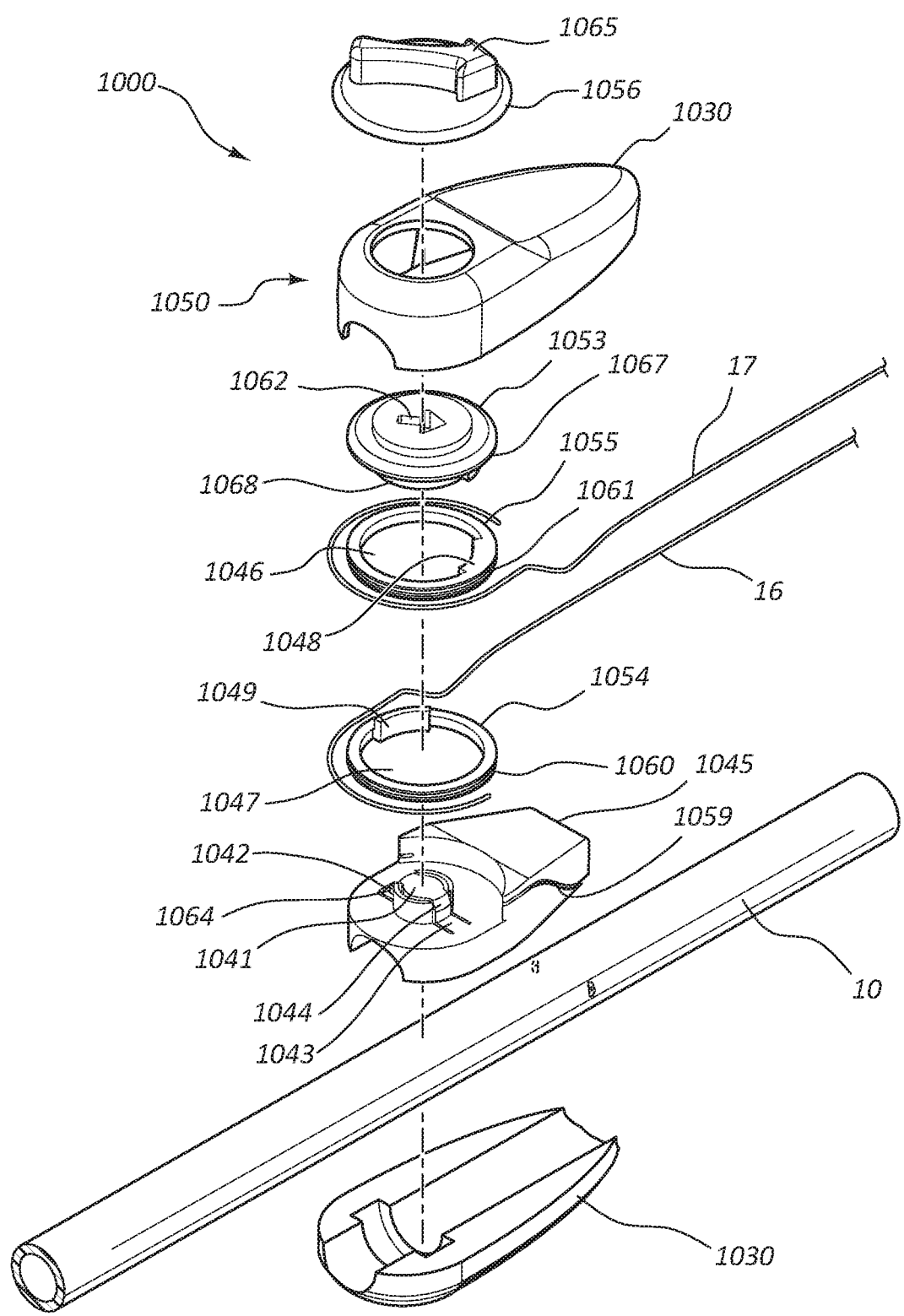
FIG. 2 is a perspective, exploded, top view of a portion of the steerable drainage device of FIG. 1.
Figure 3:
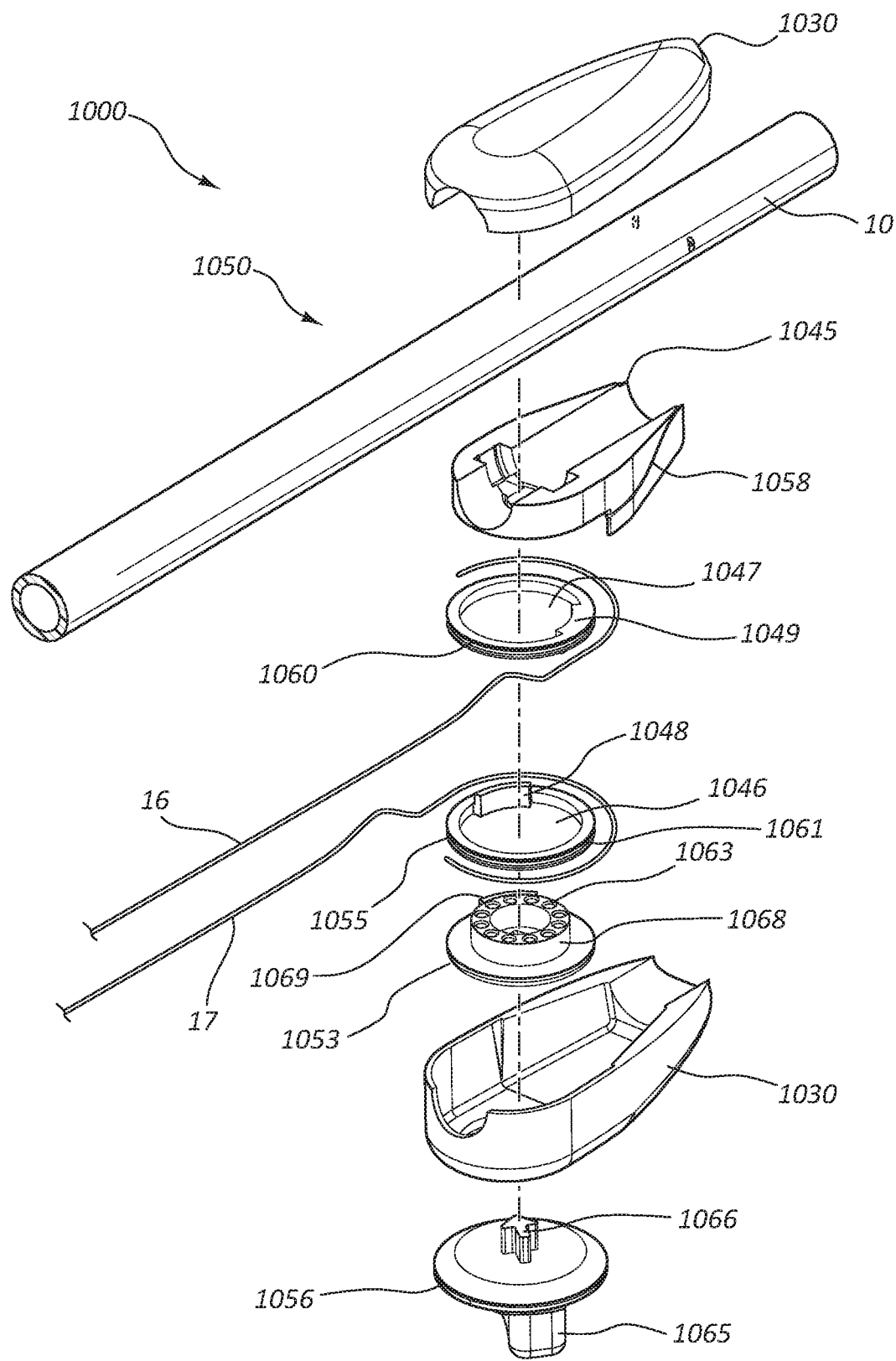
FIG. 3 is a perspective, exploded, bottom view of a portion of the steerable drainage device of FIG. 1.
Figure 4A:
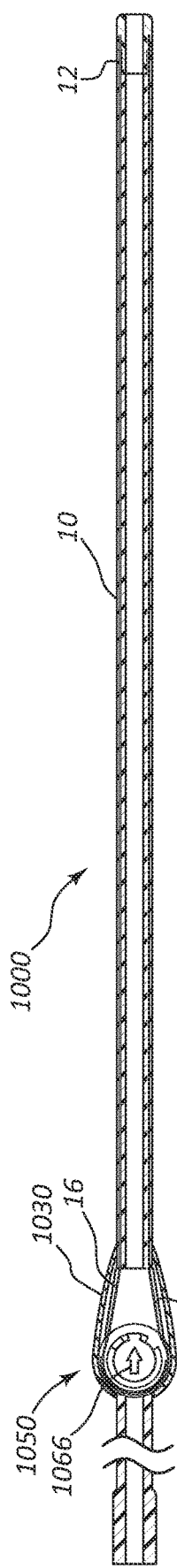
FIG. 4A is a top cross-sectional view of the steerable drainage device of FIG. 1 in a straight configuration.
Figure 4B:
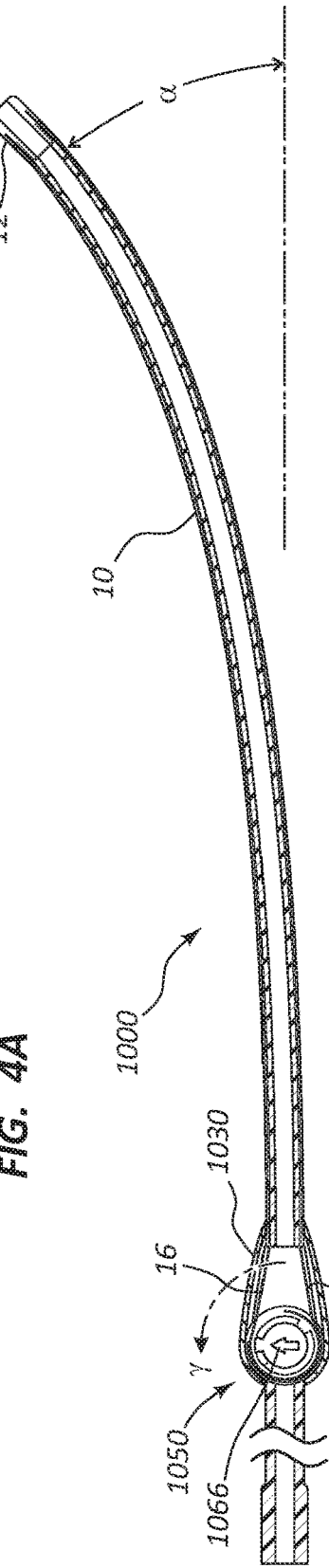
FIG. 4B is a top cross-sectional view of the steerable drainage device of FIG. 1, where the device is bent in a first direction.
Figure 4C:
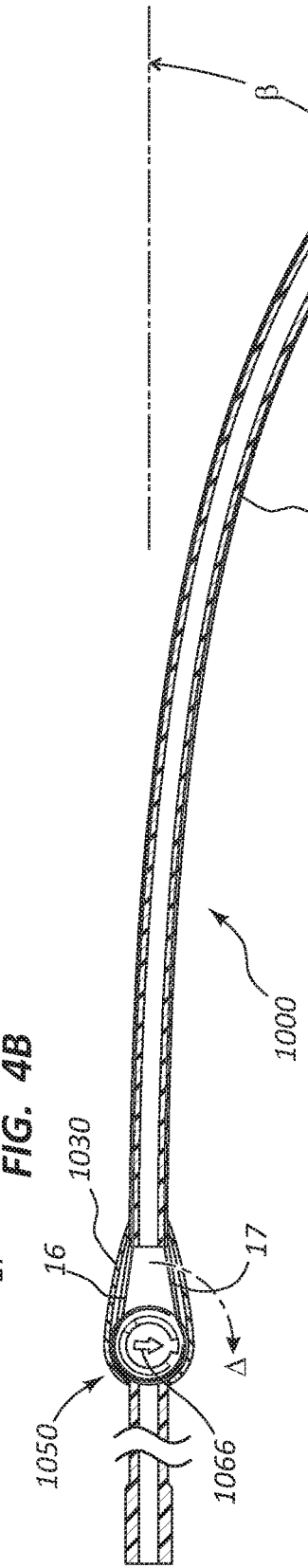
FIG. 4C is a top cross-sectional view of the steerable drainage device of FIG. 1, where the device is bent in a second direction.
Figure 5:
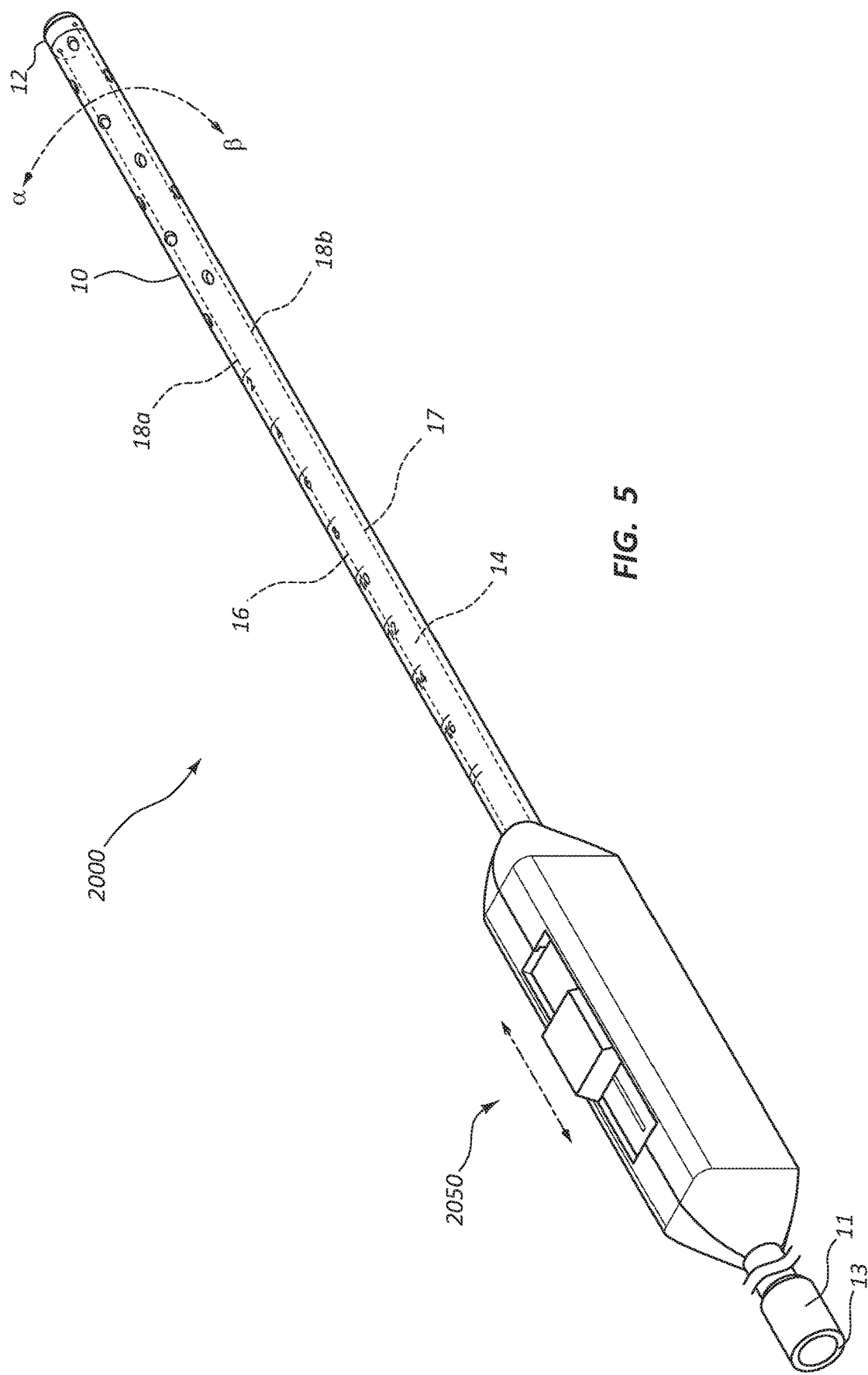
FIG. 5 is a perspective view of a steerable drainage device.

The knob 1056 may be configured to be gripped by a hand of a healthcare worker such that the knob 1056 may be rotated in a first direction and a second direction. As detailed below, the knob 1056 may be configured to lock or maintain a rotational position after rotational displacement. The knob 1056 may comprise a handle 1065 and a shaft 1066. The handle 1065 may be shaped in any suitable shape to be gripped by the healthcare worker. For example, as illustrated in FIG. 2, the handle 1065 may be in the shape of an arrow such that the knob 1056 may be gripped by the healthcare worker and may indicate a direction the drainage tube 10 may be bent. The shaft 1066 may be keyed to match with a passage 1062 through the drive capstan 1053 such that when the knob 1056 is rotated in first $\gamma$ and second directions A (as shown in FIG. 1), the drive capstan 1063 is rotated in the same directions. For example, as illustrated in FIGS. 2-3, the shaft 1066 is in a shape of an arrow and the passage 1062 through the drive capstan 1053 has a similar shape such that rotation of the knob 1056 causes rotation of the drive capstan 1053 in the same direction.

The knob 1056 may be configured to be removable from the tension control member 1050 following rotation and locking of the tension control member 1050, wherein the distal end 12 of the drainage tube 10 is maintained in an arcuate configuration. By removing the knob 1056, the patient or non-healthcare worker cannot change the curvature of the drainage tube 10 by rotating the tension control member 1050 once it has been set by the healthcare worker.

The drive capstan 1053 may comprise a disk 1067 and a cylinder 1068 extending from the disk 1067. The drive capstan 1053 may be circular in shape. In the illustrated embodiment, the keyed passage 1062 is configured to pass through the disk 1067. The cylinder 1068 can be sized to be received within a first central passage 1047 of the first spool 1054 and within a second central passage 1046 of the second spool 1055. A drive tab 1069 may extend radially outward from the cylinder 1068 and be configured to couple with a first rotation tab 1049 of the first spool 1054 and a second rotation tab 1048 of the second spool 1055. A lower end of the cylinder 1068 may comprise a plurality of recesses 1063 disposed in a wall of the cylinder 1068. The recesses 1063 may be configured to be releasably coupled to a peg 1064 of the locking member 1051 such that the tension control member 1050 may be locked in a rotated configuration.

In the illustrated embodiment, the first spool 1054 is circular in shape and comprises the first central passage 1047, a first groove 1060, and the first rotation tab 1049. The first central passage 1047 is sized to receive the cylinder 1068 of the drive capstan 1053. The first groove 1060 may be disposed around a periphery of the first spool 1054 and be sized to receive the first wire 16. The first rotation tab 1049 may extend radially inward into the first central passage 1047 and extend downward from the first spool 1054. In the embodiment of FIGS. 2 and 3, the first rotation tab 1049 is configured to couple with the drive tab 1069 of the drive capstan 1053 and the second rotation tab 1048 of the first spool as the tension control member 1050 is rotated in the first direction γ. The first wire 16 may be coupled to the first spool 1054 utilizing any suitable technique.

As shown in FIGS. 2 and 3, the second spool 1055 is circular in shape and comprises the second central passage 1046, a second groove 1061, and the second rotation tab 1048. The second central passage 1046 is sized to receive the cylinder 1068 of the drive capstan 1053. The second groove 1061 is disposed around a periphery of the second spool 1055 and is sized to receive the second wire 17. The second rotation tab 1048 extends radially inward into the second central passage 1046 and extends upward from the second spool 1055. The second rotation tab 1048 is configured to couple with the drive tab 1069 of the drive capstan 1053 and the first rotation tab 1049 of the first spool 1054 as the tension control member 1050 is rotated in the second direction Δ. The second wire 17 may be coupled to the second spool 1055 utilizing any suitable technique.

In some embodiments, the locking member 1051 comprises a body 1045. The body 1045 may comprise a first channel 1058, a second channel 1059, and a locking arm 1044. The first channel 1058 may be disposed on one side of the body 1045 and be sized to slideably receive the first wire 16. The first channel 1058 may be configured to direct the first wire 16 from one closed lumen 18 of the drainage tube 10 to the first groove 1060 of the first spool 1054 such that the first wire 16 at least partially wraps around the first spool 1054 in a first direction. The second channel 1059 may be disposed on an opposing side of the body 1045 and be sized to slideably receive the second wire 17. The second channel 1059 may be configured to direct the second wire 17 from one closed lumen 18 of the drainage tube 10 to the second groove 1061 of the second spool 1055 such that the second wire 17 at least partially wraps around the second spool 1055.

In the illustrated embodiment the locking arm 1044 comprises a first segment 1043, an end segment 1042, and a button 1041. The locking arm 1044 is configured as a cantilevered beam such that the locking arm 1044 extends across the body 1045. An end of the first segment 1043 is coupled to the body 1045, and sides of the first segment 1043 may be moveable relative to the body 1045. The button 1041 is disposed between the first segment 1043 and the end segment 1042 and extend upward from the locking arm 1044. An upper portion of the button 1041 is configured to be depressible by an end of the shaft 1066 of the knob 1056 such that a lower portion of the button 1041 compresses the drainage tube 10 disposed underneath the button 1041. The end segment 1042 extends laterally from the button 1041 and is configured to move relative to the body 1045. The end segment comprises the peg 1064. The peg 1064 is configured to be received and released by at least one recess 1063 of the drive capstan 1053.

In use, the steerable drainage device 1000 may be utilized to insert the drainage tube 10 into a body cavity, such as the pleural cavity to drain fluid from around the lungs. The steerable drainage device 1000 may be used to direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first α and second β directions by actuation of the tension control member 1050 such that the drainage tube 10 may be directed to the target location.

During use, the keyed shaft 1066 of the knob 1056 is inserted through the keyed passage 1062 of the drive capstan 1053 and through the first central passage 1047 of the first spool 1054 and through the second central passage 1046 of the second spool 1055. The knob 1056 is depressed against the drive capstan 1053. The end of the keyed shaft 1066 engages with the button 1041 of the locking member 1051 such that the locking arm 1044 is displaced downward and away from the drive capstan 1053. The button 1041 engages and compresses the drainage tube 10. The peg 1064 of the locking member 1051 is displaced downward and displaced from the recess 1063 of the shaft 1066 of the knob 1056 such that the tension control member 1051 is unlocked and is rotatable by the healthcare worker.

The handle 1065 of the knob 1056 is grasped by the healthcare worker and rotated in the first direction γ. Rotation of the knob 1056 in the first direction γ causes the drive capstan 1053 to be rotated in the first direction γ due to the keyed coupling of the keyed shaft 1066 with the keyed passage 1062. The drive tab 1069 of the drive capstan 1053 engages the first rotation tab 1049 of the first spool 1054 such that the first spool 1054 is rotated in the first direction γ. Rotation of the first spool 1054 results in the first wire 16 sliding proximally through the first channel 1058 of the body 1045 and being received in the first groove 1060 such that the first wire 16 is at least partially wrapped around the first spool 1054. As a result of this rotation, a tension force is applied to the first wire 16. The tension force in turn, compresses the drainage tube 10 along the side of the drainage tube 10 where the first wire 16 is disposed. Compression of the drainage tube 10 causes the distal end 12 to bend in the first direction α, forming an arcuate shape in a single plane. The drainage tube 10 may be bent from about one degree to about 180 degrees or more in the first direction α.

The curved drainage tube 10 may be further advanced into the body cavity and directed to the target location. Adjustments to the amount of curvature of the drainage tube 10 are accomplished by further rotation of the knob 1056 in the first direction γ to apply a greater tension force and to achieve more curvature of the drainage tube 10 or by rotation of the knob 1056 in the second direction Δ to achieve less curvature or curvature in the second direction. Rotation of the knob 1056 in the second direction Δ may release the tension force from the first wire 16 and apply the tension force to the second wire 17. Rotation of the knob 1056 in the second direction Δ causes the drive tab 1069 to engage the second rotation tab 1048 of the second spool 1055, resulting in rotation of the second spool 1055 in the second direction Δ. The second wire 17 may slide through the second channel 1059 in a proximal direction and be received in the second groove 1061 as the second wire 17 is at least partially wrapped around the second spool 1055. The tension force applied to the second wire 17 compresses the drainage tube 10 along the side of the drainage tube 10 where the second wire 17 is disposed such that the drainage tube 10 is bent in the second direction β, forming an arcuate shape in a single plane. The drainage tube 10 may be bent from about one degree to about 180 degrees in the second direction β.

As tension is applied to the second wire 17, tension may be removed from the first wire 16. The first wire 16 may be displaced distally and unwrap from the first spool 1054 as the drainage tube 10 is straightened and/or bent in the second direction β. The tension control member 1050 may or may not apply a push force to the first wire 16. The first spool 1054 and the second spool 1055 may be configured to rotate separately such that rotation of one spool in the first γ or second Δ direction does not cause the other spool to be rotated in the same direction to the same degree of rotation.

After rotation, adjustment, or placement, downward pressure on the knob 1056 may be released and the knob 1056 may be removed by the healthcare worker. Upon release of the downward pressure, the button 1041 of the locking arm 1044 may be forced upward by the resiliency of the drainage tube 10. The peg 1064 of the locking arm 1044 may be disposed into one of the plurality of recesses 1063 of the drive capstan 1053 such that the tension control member 1050 is in a rotationally locked configuration and the drainage tube 10 is maintained in an arcuate configuration.

FIGS. 5-7C depict an embodiment of a steerable drainage device 2000 that resembles the steerable drainage device 1000 described above in certain respects. Accordingly, like features are designated with like reference numerals, with the leading digit incremented to "2." For example, the embodiment depicted in FIGS. 5-7C includes a tension control member 2050 that may, in some respects, resemble the tension control member 1050 of FIGS. 1-4C. Relevant disclosure set forth above regarding similarly identified features thus may not be repeated hereafter. Moreover, specific features of the steerable drainage device 1000 and related components shown in FIGS. 1-4C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the steerable drainage device 2000 and related components depicted in FIGS. 5-7C. Any suitable combination of the features, and variations of the same, described with respect to the steerable drainage device 1000 and related components illustrated in FIGS. 1-4C can be employed with the steerable drainage device 2000 and related components of FIGS. 5-7C, and vice versa. This pattern of disclosure applies equally to further embodiments depicted in subsequent figures and described hereafter, wherein the leading digits may be further incremented. Elements, such as 10, 16, 17, etc. that have the same number for each of the described embodiments are meant to illustrate similarity in disclosed steerable drainage devices but not meant to imply that the elements are necessarily the same tube, wire, etc.

Each disclosed embodiment of the steerable drainage device may comprise a particular mechanism configured to apply tension to wires and bend an end of a tube in two directions but disclosure about application of the various embodiments in use is analogous to all disclosed embodiments.

Figure 6:
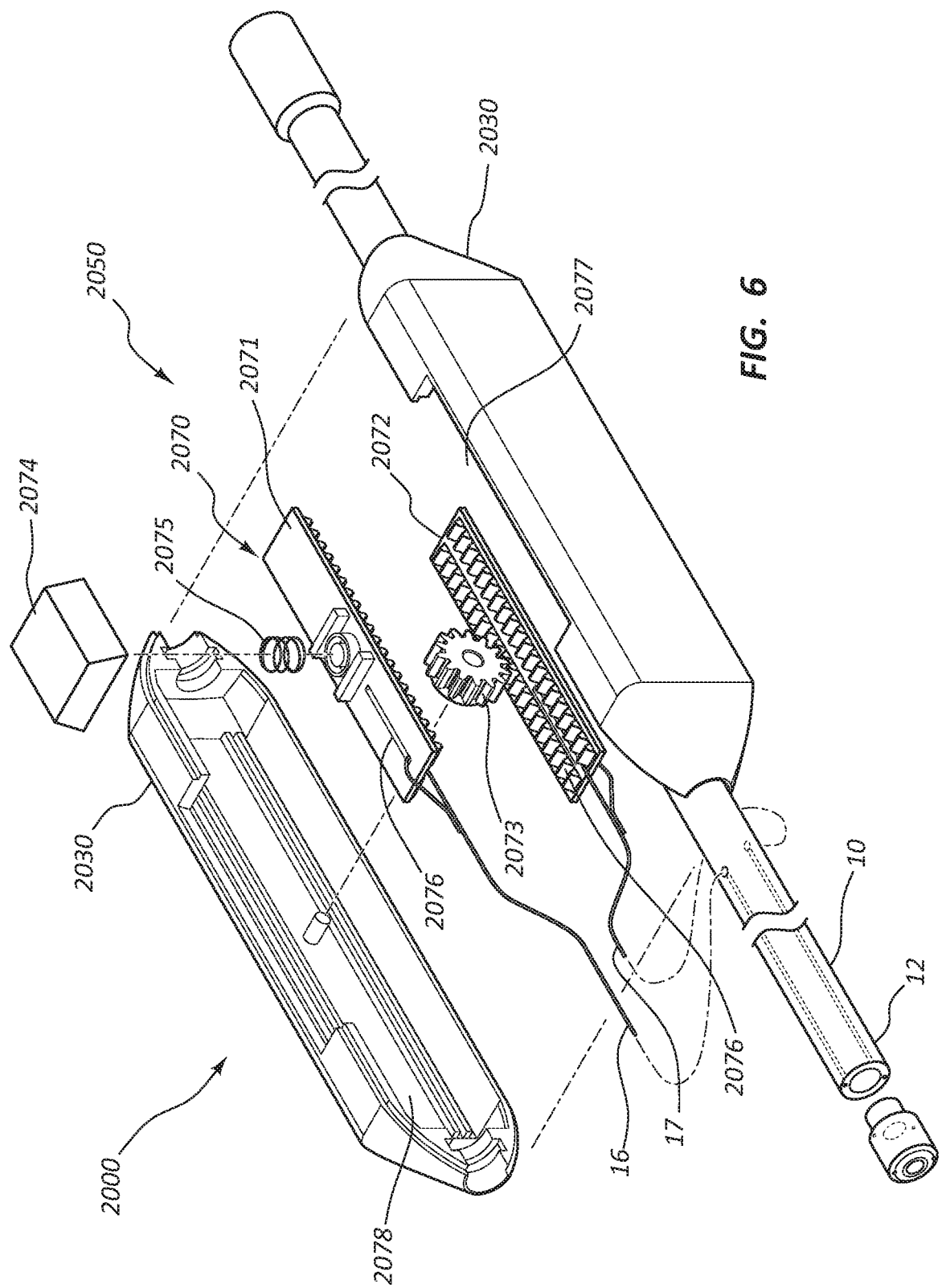
FIG. 6 is a perspective, exploded, view of the steerable drainage device of FIG. 5.
Figure 8:
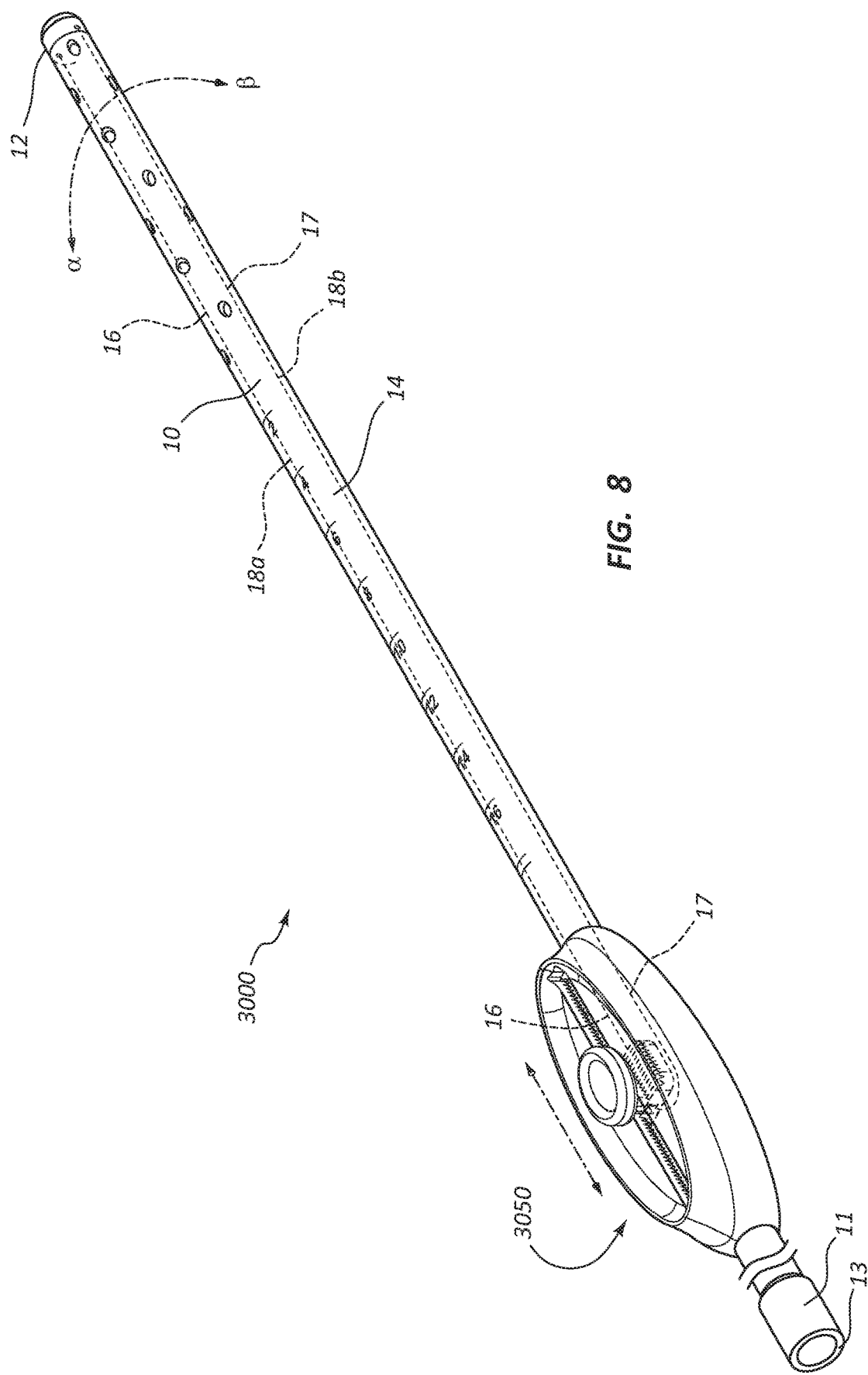
FIG. 8 is a perspective view of a steerable drainage device.
Figure 11:
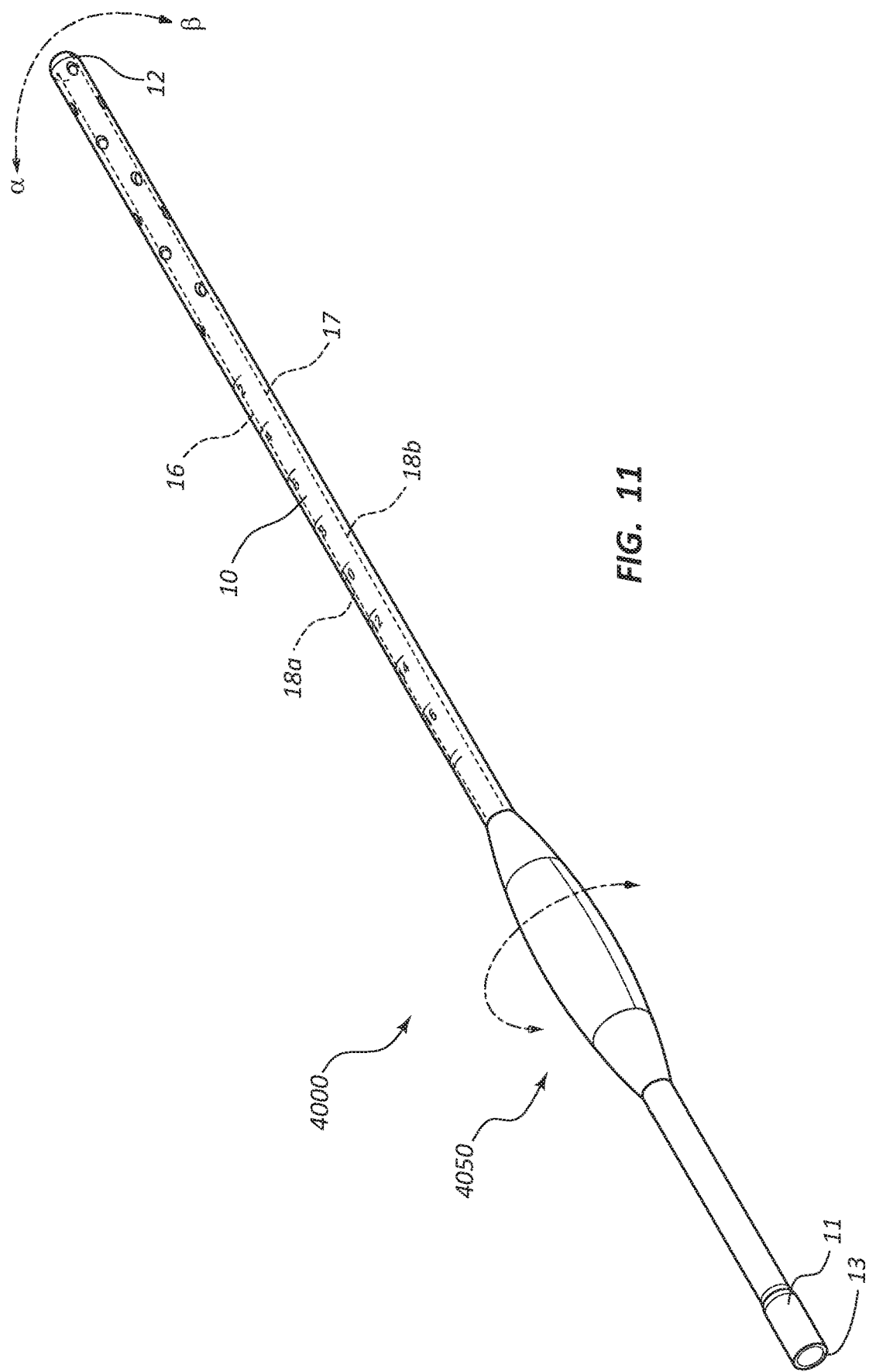
FIG. 11 is a perspective view of a steerable drainage device.
Figure 13A:
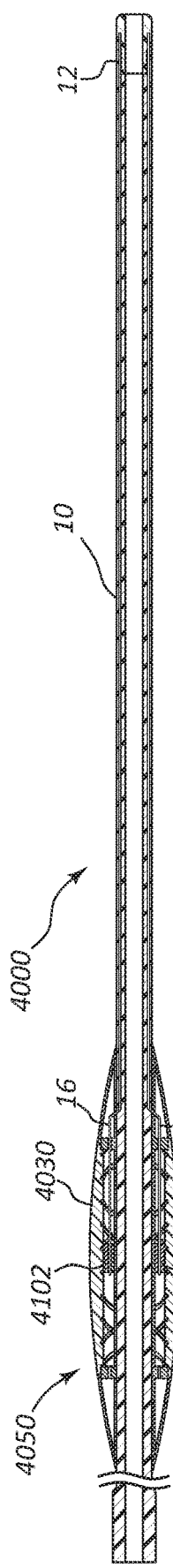
FIG. 13A is a top cross-sectional view of the steerable drainage device of FIG. 11 in a straight configuration.
Figure 13B:
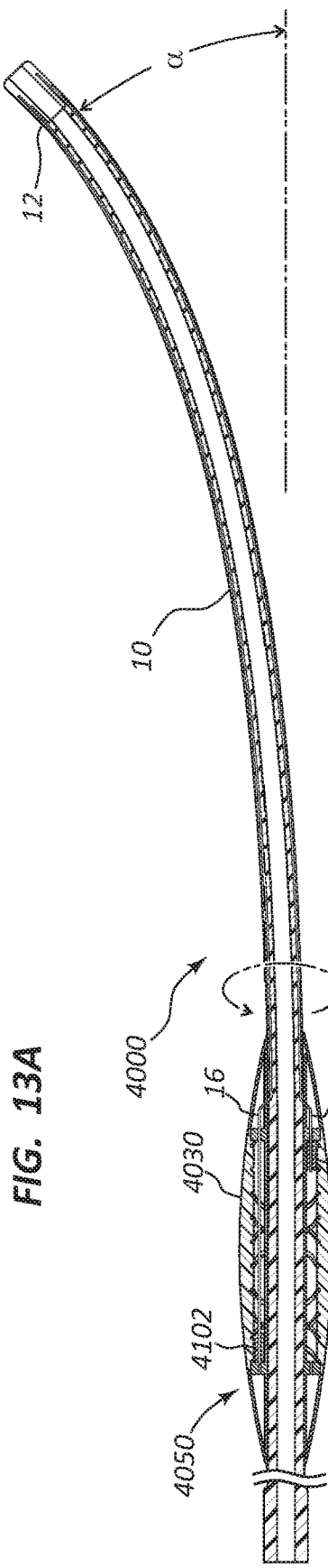
FIG. 13B is a top cross-sectional view of the steerable drainage device of FIG. 11, where the device is bent in a first direction.
Figure 13C:
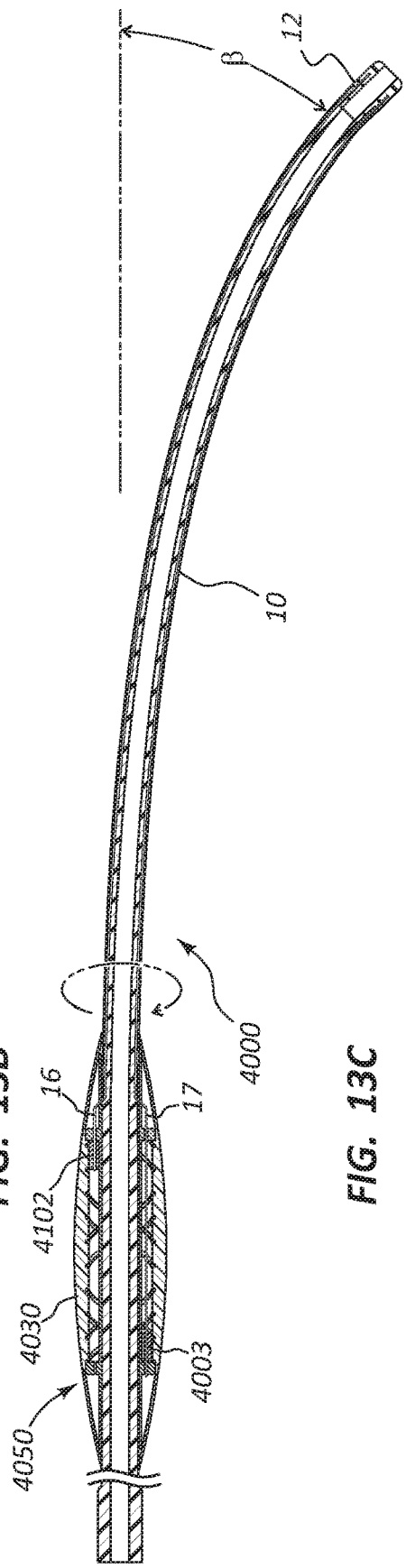
FIG. 13C is a top cross-sectional view of the steerable drainage device of FIG. 11, where the device is bent in a second direction.
Figure 14:
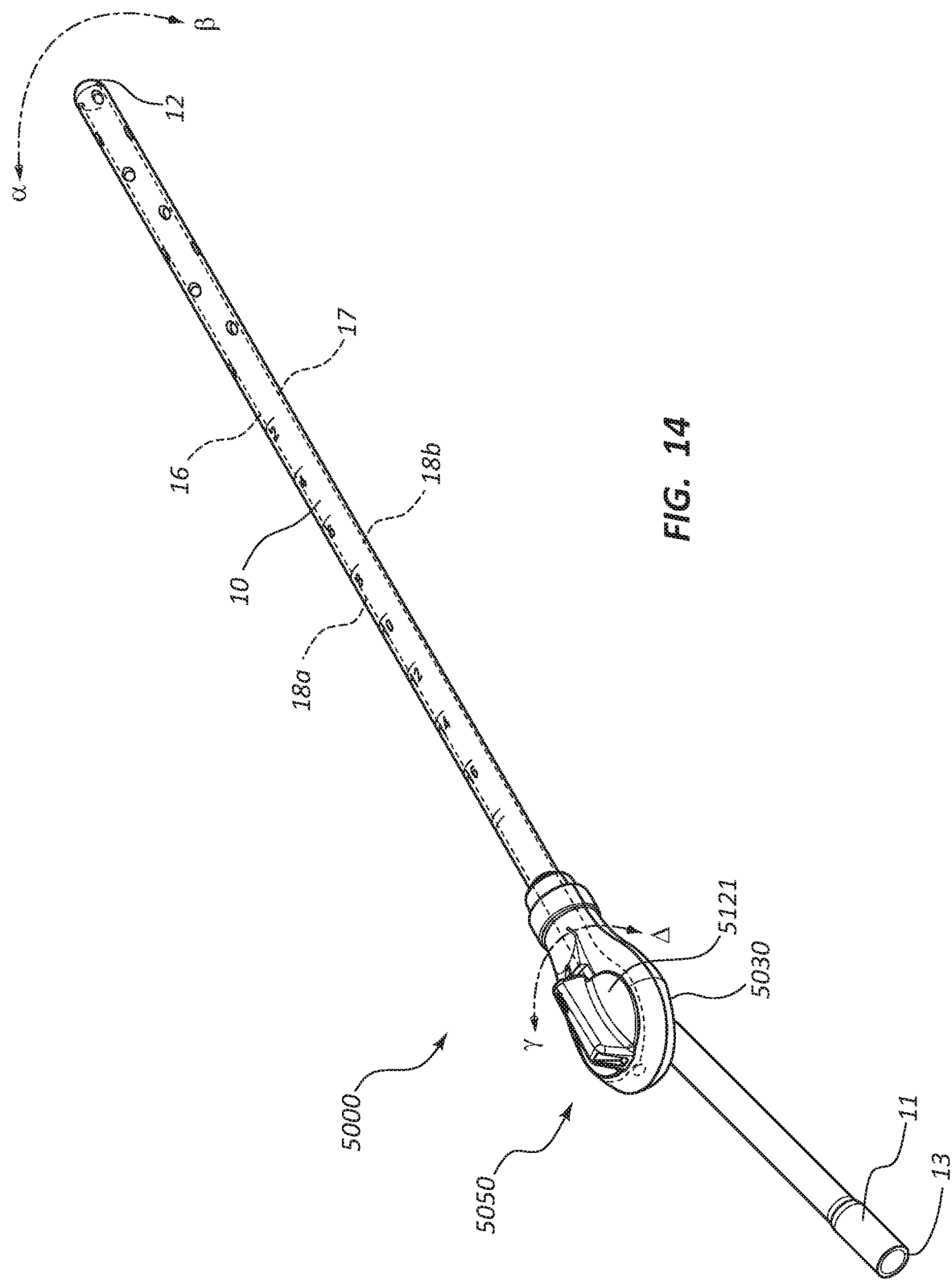
FIG. 14 is a perspective view of a steerable drainage device.
Figure 15:
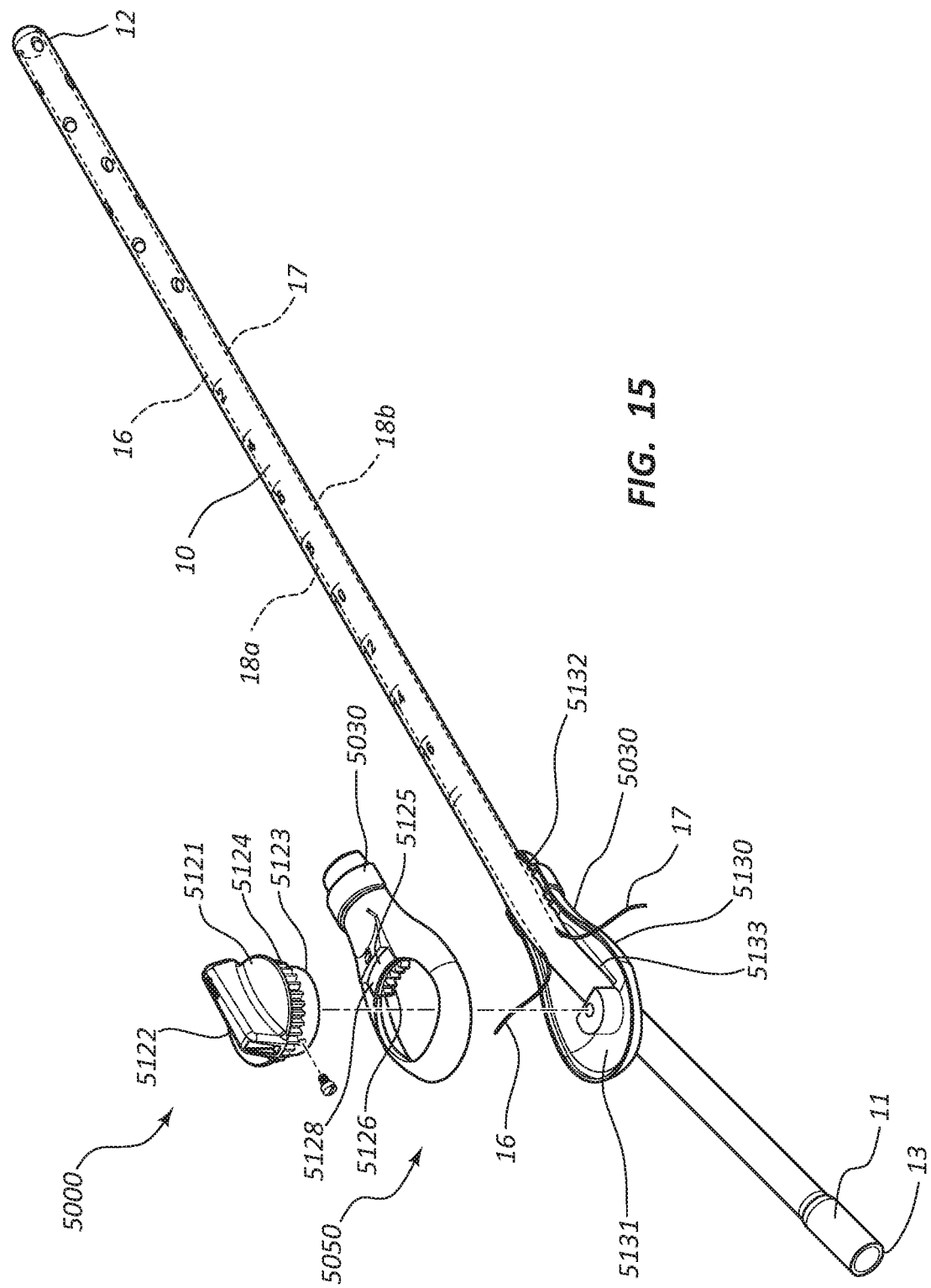
FIG. 15 is a perspective, exploded, view of the steerable drainage device of FIG. 14.
Figure 16A:
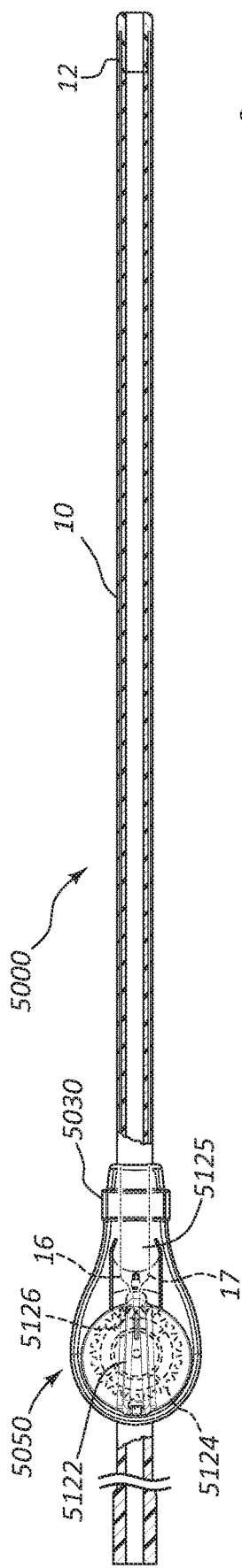
FIG. 16A is a top partial cross-sectional view of the steerable drainage device of FIG. 14 in a straight configuration.
Figure 16B:
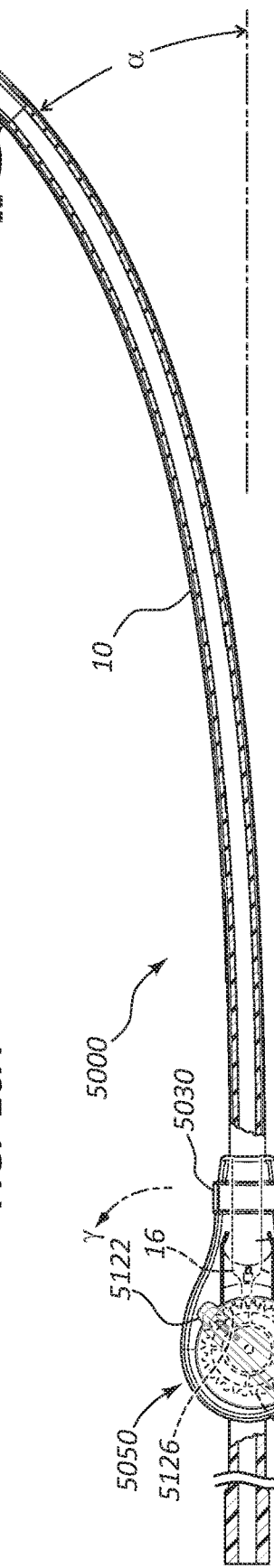
FIG. 16B is a top partial cross-sectional view of the steerable drainage device of FIG. 14, where the device is bent in a first direction.
Figure 16C:
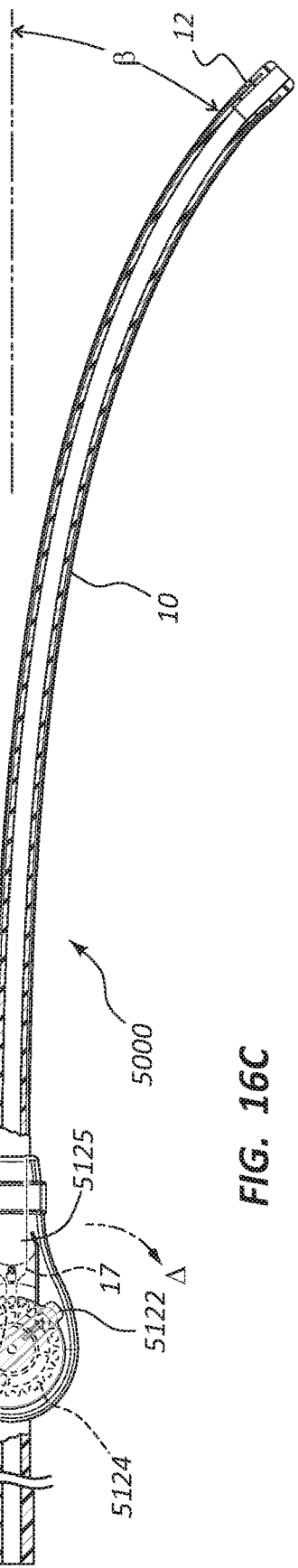
FIG. 16C is a top partial cross-sectional view of the steerable drainage device of FIG. 14, where the device is bent in a second direction.
Figure 17:
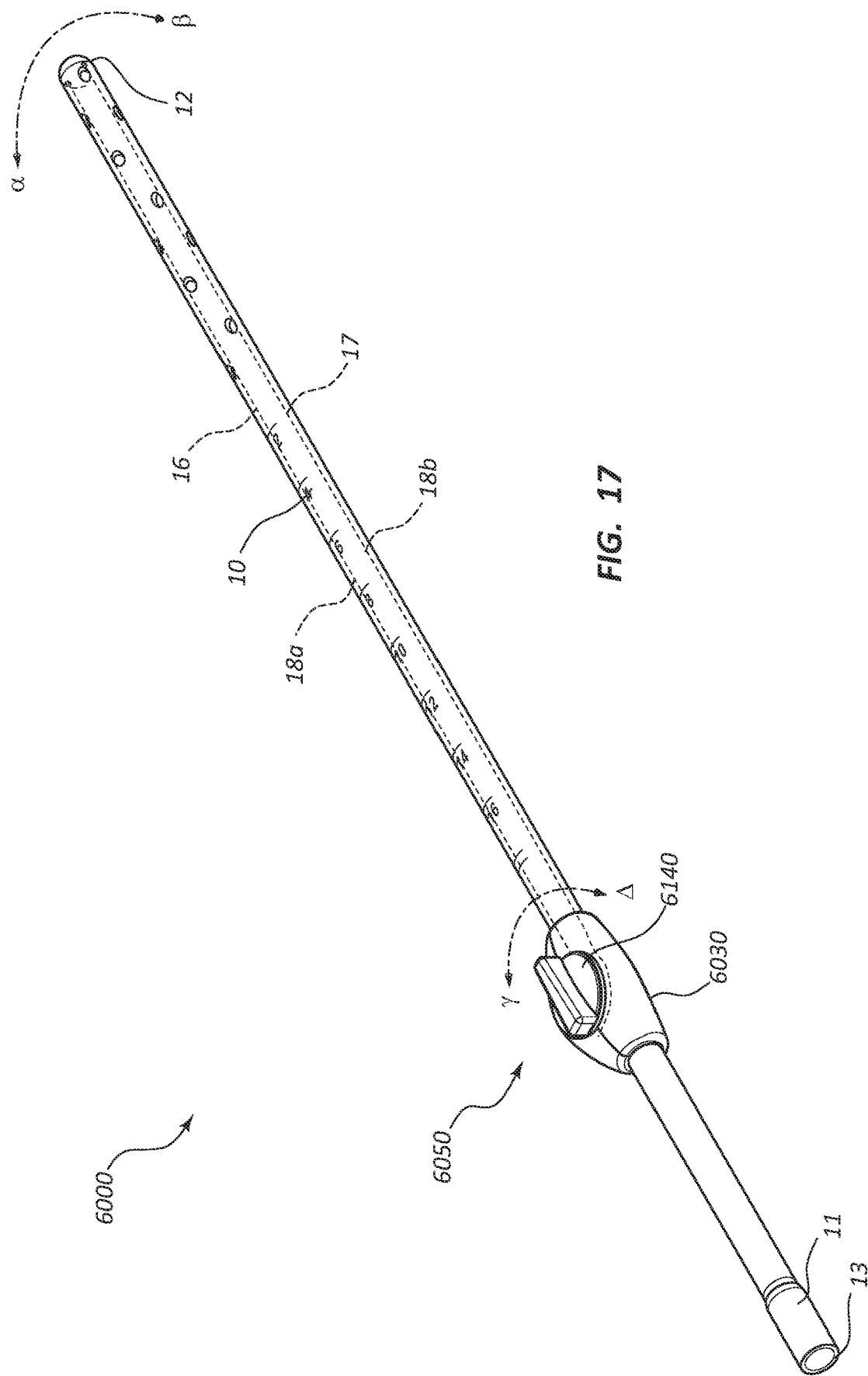
FIG. 17 is a perspective view of a steerable drainage device.
Figure 19A:
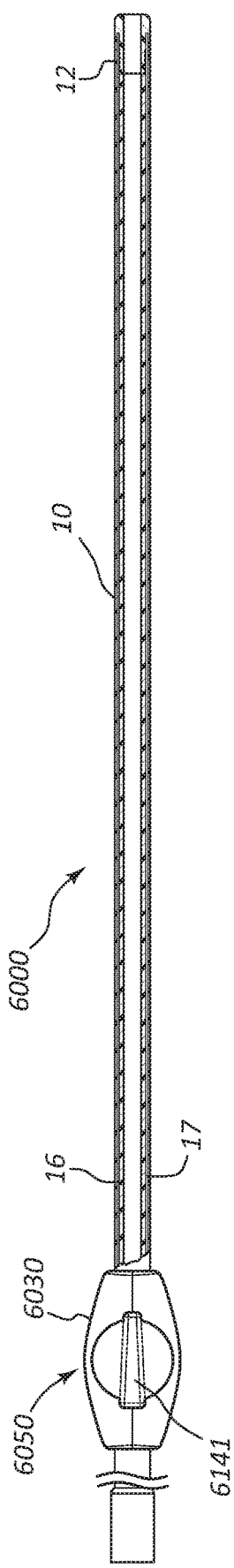
FIG. 19A is a top partial cross-sectional view of the steerable drainage device of FIG. 17 in a straight configuration.
Figure 19B:
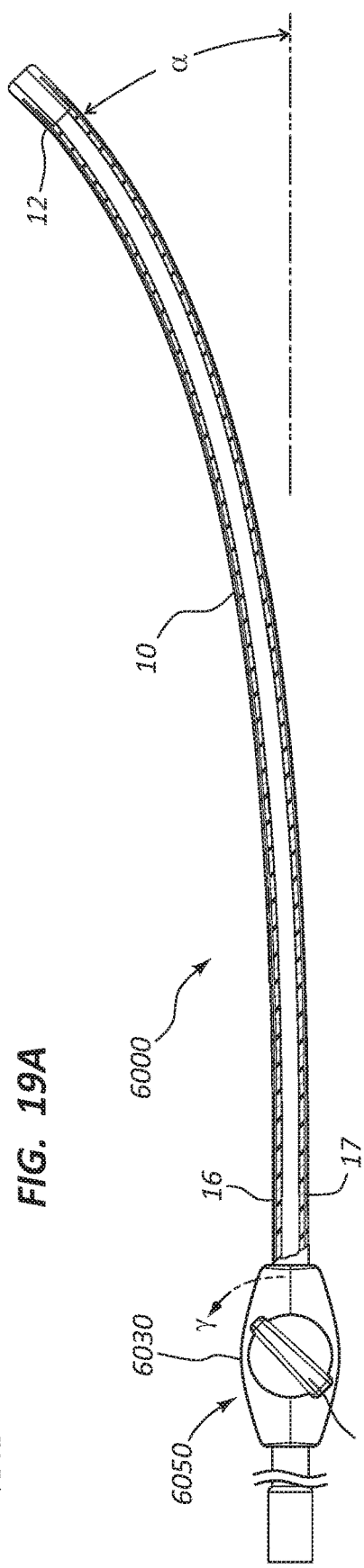
FIG. 19B is a top partial cross-sectional view of the steerable drainage device of FIG. 17, where the device is bent in a first direction.
Figure 19C:
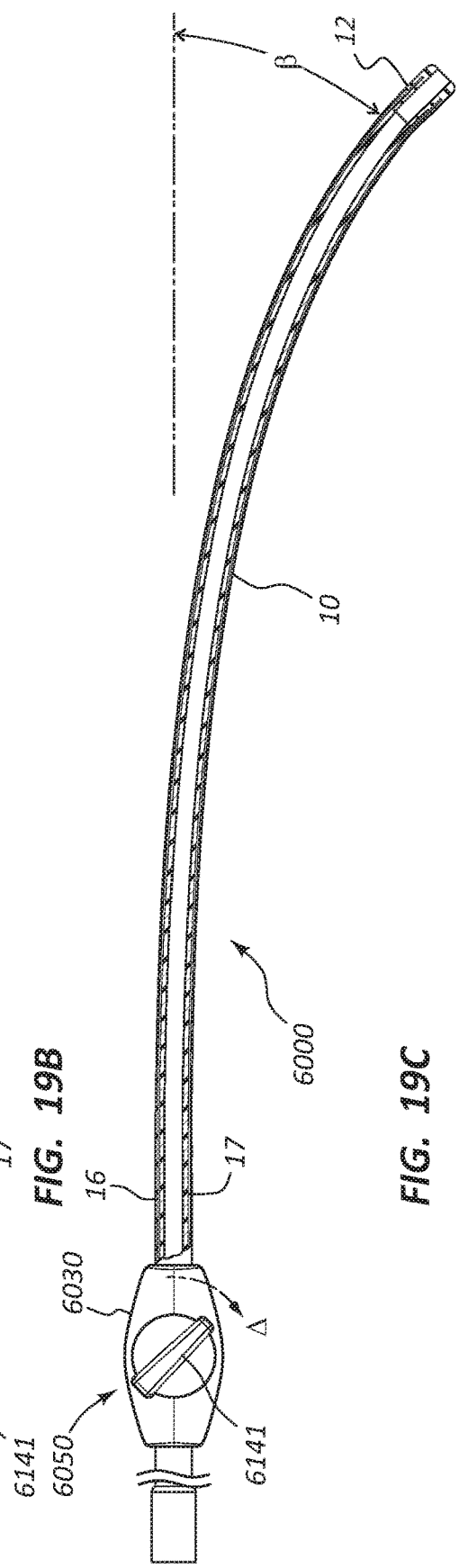
FIG. 19C is a top partial cross-sectional view of the steerable drainage device of FIG. 17, where the device is bent in a second direction.
Figure 20:
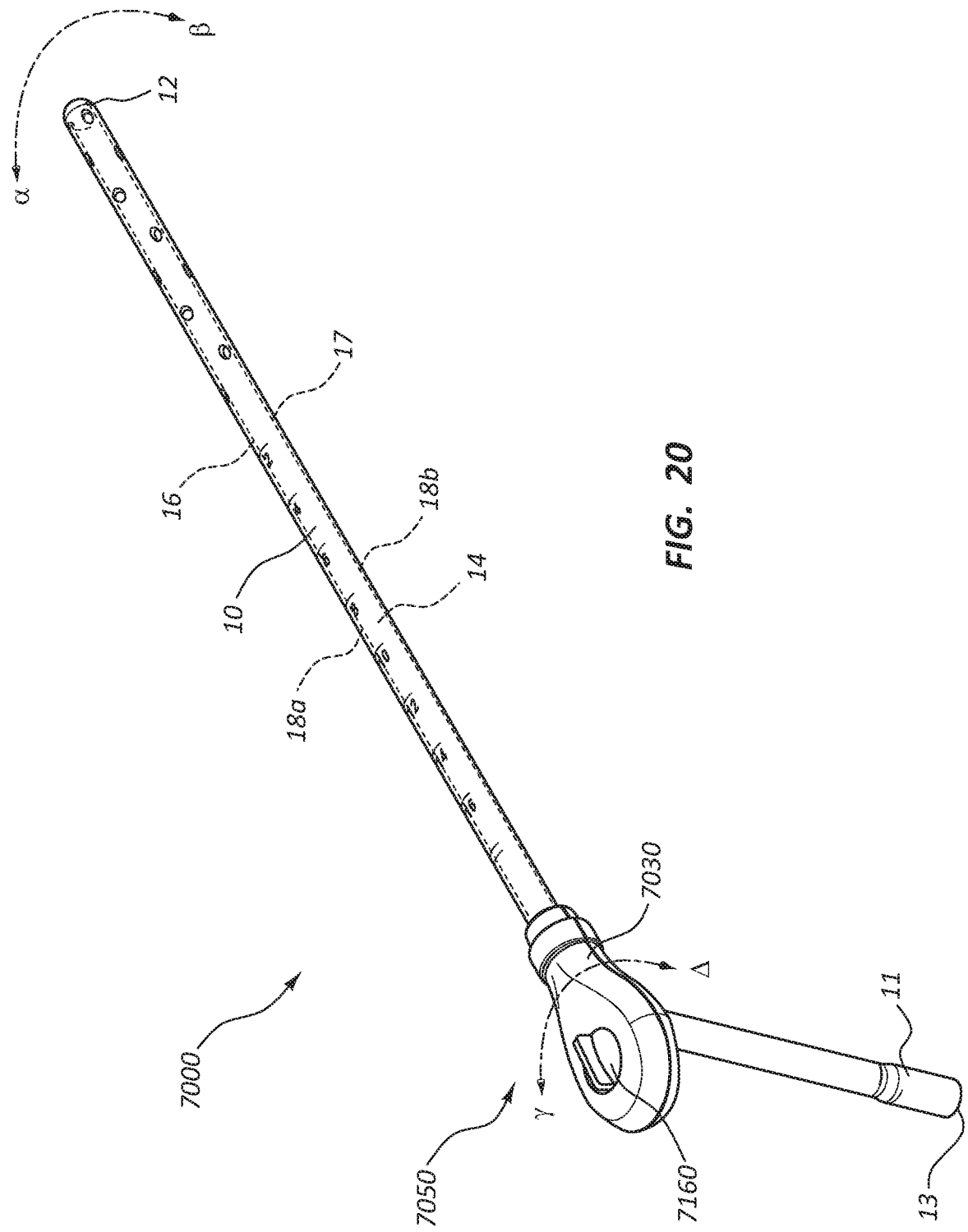
FIG. 20 is a perspective view of a steerable drainage device.

Referring to FIGS. 5-7C, the steerable drainage device 2000 comprises the drainage tube 10 as previously described and a tension control member 2050 disposed adjacent the proximal end 11 of the drainage tube 10. The tension control member 2050 comprises a housing 2030, a button 2074 and a linear displacement mechanism 2070. The housing 2030 may be configured to be grasped or held by the hand of a healthcare worker. As illustrated in FIG. 6, the housing 2030 comprises a longitudinal passage 2078 with openings at a proximal end and a distal end such that the drainage tube 10 is partially disposed within the passage 2078. The housing 2030 comprises a left half and a right half. The two halves may be separate components and coupled together using any suitable technique, or the two halves may be coupled together with a hinge, such as a living hinge. An opening 2077 is disposed in the housing 2030.

The linear displacement mechanism 2070 comprises a first rack 2071, a second rack 2072, and a gear 2073. The gear 2073 comprises a plurality of teeth around a perimeter and is fixedly secured in a position within the passage 2078 between the first rack 2071 and the second rack 2072. The first and second racks 2071, 2072 comprise a plurality of teeth extending along a length of the racks 2071, 2072. The teeth of the racks 2071, 2072 are configured to mesh with the teeth of the gear 2073. The racks 2071, 2072 may comprise slots 2076 extending longitudinally along at least a portion of the length of the racks 2071, 2072. The slots 2076 may be configured to facilitate coupling of the first and second wires 16, 17 to the first and second racks 2071, 2072, respectively. For example, as shown in FIG. 6, proximal ends of the first and second wires 16, 17 are looped through the slots 2076.

In the illustrated embodiment, the button 2074 is operably coupled to the first rack 2071 and disposed within the opening 2077 of the housing 2030. The button 2074 has a substantially square shape and comprise walls that taper radially outward from a top surface. The walls of the button 2074 are configured to frictionally engage with matching tapered walls of the opening 2077 such that linear movement of the button 2074 is restricted. The opening 2077 is configured to retain the button 2074 at least partially within the passage 2078 of the housing 2030. For example, the width of the opening 2077 at an outer surface of the housing 2030 may be less than a width of the wall of the button 2074 at a point below a top surface of the button 2074. A biasing member 2075 is disposed between the button 2074 and the first rack 2071. The biasing member 2075 may be any resilient component, such as a coiled spring, a leaf spring, an elastomeric disk, etc.

In use, the steerable drainage device 2000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first α or second β direction by actuation of the tension control member 2050 such that the drainage tube 10 may be directed to the target location.

During use, the housing 2030 of the tension control member 2050 is grasped or held by the hand of the healthcare worker. Utilizing a suitable imaging system, such as x-ray, fluoroscopy, or ultrasound, a drainage tube 10 insertion direction may be determined. Adjustments to the insertion direction may be made by actuation of the tension control member 2050. Downward pressure on the button 2074 is applied by a finger of the healthcare worker such that the biasing member 2075 is compressed and the wall of the button 2074 released from frictional engagement with the wall of the opening 2077 of the housing 2030.

Proximal displacement of the button 2074 by the finger of the healthcare worker causes the first rack 2071 to be displaced proximally and tension to be applied to the first wire 16 such that the distal end 12 of the drainage tube 10 is bent in a first direction α. Proximal displacement of the first rack 2071 results in rotation of the gear 2073 and distal displacement of the second rack 2072 as the teeth of the gear 2073 and the racks 2071, 2072 mesh.

Distal displacement of the button 2074 by the finger of the healthcare worker causes the first rack 2071 to be displaced distally and the second rack 2072 to be displaced proximally as the gear 2073 is rotated such that tension is applied to the second wire 17. The tension on the second wire 17 causes the distal end 12 of the drainage tube 10 to be bent in a second direction β. Distal displacement of the first rack 2071 may result in rotation of the gear 2073 in a second direction and proximal displacement of the second rack 2072 as the teeth of the gear 2073 and the racks 2071, 2072 mesh.

With continued use, downward pressure on the button 2074 is released and the biasing member 2075 is decompressed. The button 2074 is displaced upward such that the wall of the button 2074 may frictionally engage the wall of the opening 2077. The button 2074 may be locked in a longitudinal position such that the distal end 12 of the drainage tube 10 remains bent in either the first α or second direction β.

FIGS. 8-10C illustrate a steerable drainage device 3000 comprising the drainage tube 10 as previously described and a tension control member 3050 disposed adjacent the proximal end 11 of the drainage tube 10. In the illustrated embodiment, the tension control member 3050 comprises a housing 3030, a button 3080, a distal pulley 3082, and a proximal pulley 3083. The housing 3030 is configured to be grasped or held by the hand of a healthcare worker. The housing 3030 comprises a longitudinal passage 3086 with openings at a proximal end and a distal end such that the drainage tube 10 may be partially disposed within the passage 3086 and in alignment with a longitudinal axis of the housing 3030. The housing 3030 comprises a left half and a right half. The two halves may be separate components and coupled together using any suitable technique, or the two halves may be coupled together with a hinge, such as a living hinge. A longitudinal slot 3087 is disposed in a top portion of the housing 3030. A plurality of downwardly directed teeth 3081 extend along at least a portion of the periphery of the slot 3087.

As shown in FIGS. 9A and 9B, the button 3080 comprises an upper portion 3088, a shaft 3085, and a lower portion 3084. The upper portion 3088 may be substantially circular or oblong in shape. The upper portion 3088 is configured to be slideably disposed within a recess 3094 of the housing 3030. The upper portion 3088 may be configured to be engaged by a finger of a healthcare worker to depress and slide the button 3080 proximally and distally relative to the housing 3030. The upper portion 3088 may comprise any suitable grip enhancing feature, such as bumps, recesses, surface texturing, elastomeric layer, etc.

The shaft 3085 extends from a bottom surface of the upper portion 3088. The shaft 3085 is sized to be longitudinally displaceable within the slot 3087 of the housing 3030. The first and second wires 16, 17 may be coupled to the shaft 3085 using any suitable technique. For example, the shaft 3085 may comprise a wire passage 3091. The first wire 16 may pass through the passage 3091 proximally. An end of the first wire 16 may comprise a crimp, weld bead, etc. such that the end of the first wire 16 may be prevented from passing back through the passage 3091. In a similar manner, the second wire 17 may pass through the passage 3091 distally. An end of the second wire 17 may comprise a crimp, weld bead, etc. such that the end of the second wire 17 may be prevented from passing back through the passage 3091.

The lower portion 3089 is coupled to the shaft 3085. The lower portion 3089 comprises a plurality of upwardly directed teeth 3090 disposed on lateral sides of the lower portion 3084. The teeth 3090 are configured to mesh with the teeth 3081 of the housing 3030.

In the illustrated embodiment, the distal pulley 3082 is disposed adjacent a distal end of the passage 3086. The proximal pulley 3083 is disposed adjacent a proximal end of the passage 3086. The distal and proximal pulleys 3082, 3083 are configured to direct the first and second wires 16, 17, respectively, to the button 3080. For example, the first wire 16 may pass around the distal pulley 3082 such that the first wire 16 may be coupled to a distal side of the button 3080. The second wire 17 may pass around the proximal pulley 3083 such that the second wire 17 may be coupled to a proximal side of the button 3080.

In use, the steerable drainage device 3000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first α and second β directions by actuation of the tension control member 3050 such that the drainage tube 10 may be directed to the target location.

During use, the housing 3030 of the tension control member 3050 may be grasped or held by the hand of the healthcare worker. Utilizing a suitable imaging system, such as x-ray, fluoroscopy, or ultrasound, a drainage tube 10 insertion direction may be determined. Adjustments to the insertion direction may be made by actuation of the tension control member 3050. Downward pressure on the button 3080 may be applied by a finger of the healthcare worker such that the button 3080 is displaced downward. The teeth 3090 of a lower portion 3089 may unmesh from the teeth 3081 of the housing 3030 such that the button 3080 may be longitudinally slideable. Additionally, a bottom surface of the lower portion 3089 may engage with a wall of the drainage tube 10 and compress the drainage tube 10.

Proximal displacement of the button 3080 by the finger of the healthcare worker causes tension to be applied to the first wire 16 such that the distal end 12 of the drainage tube 10 is bent in a first direction α. Distal displacement of the button 3080 by the finger of the healthcare worker causes tension to be applied to the second wire 17 such that the distal end 12 of the drainage tube 10 is bent in a second direction β.

During continued use, downward pressure on the button 3080 is released and the drainage tube 10 is decompressed. The button 2080 is biased upward such that the teeth 3090 of the lower portion 3089 mesh with the teeth 3081 of the housing 3030. The button 2080 is locked in a longitudinal position such that the distal end 12 of the drainage tube 10 remains bent in either the first or second direction.

FIGS. 11-13C illustrate a steerable drainage device 4000 comprising the drainage tube 10 as previously described and a tension control member 4050 disposed adjacent the proximal end 11 of the drainage tube 10. The tension control member 4050 comprises a housing 4030, an inner shaft 4101, a first nut 4102, a second nut 4103, and end caps 4110.

In the illustrated embodiment, the inner shaft 4101 comprises a passage 4111, rails 4109, channels 4108, and flanges 4112. The inner shaft 4101 may be substantially a hollow cylinder. The drainage tube 10 is disposed through the passage 4111 such that the drainage tube 10 extends beyond a proximal end and a distal end of the inner shaft 4101 and is longitudinally aligned with a longitudinal axis of the inner shaft 4101. The inner shaft 4101 is fixedly coupled to the drainage tube 10. Two or more rails 4109 are disposed opposing one another on an outer surface of the inner shaft 4101. The rails 4109 extend longitudinally along at least a portion of the length of the inner shaft 4101. Channels 4108 are disposed in the outer surface of the inner shaft 4101 adjacent the rails 4109. The channels 4108 extend longitudinally along the length of the rails 4109. Flanges 4112 are disposed at a proximal end and a distal end of the rails 4109. The flanges 4112 extend radially outward from the outer surface of the inner shaft 4101.

The first nut 4102 and the second nut 4103 are operably coupled to the inner shaft 4101. The nuts 4102, 4103 may be formed in a semi-circular shape. The nuts 4102, 4103 comprise a tab 4113 configured to be slideably disposed within the channels 4108. The nuts 4102, 4103 are disposed on the inner shaft 4101 such that they oppose one another on the sides of the inner shaft 4101. The nuts 4102, 4103 comprise an external, male thread 4104. The male thread 4104 of the first nut 4102 is be oriented in a clockwise direction. The male thread 4104 of the second nut 4103 is oriented in a counterclockwise direction. The nuts 4102, 4103 are configured to be coupled to the wires 16, 17 in any suitable manner. For example, the nuts 4102, 4103 and the flanges 4112 may comprise small wire passages 4115. The wires 16, 17 may pass through the wire passages 4115. To prevent removal of the wires 16, 17, a crimp, weld bead, etc. may be formed on the end of the wires 16, 17 such that a diameter of the end of the wires 16, 17 is larger than a diameter of the wire passages 4115.

In the embodiment of FIGS. 12 and 12A, the housing 4030 may be configured to be grasped and rotated by the hand of a healthcare worker. The housing 4030 comprises a left half and a right half substantially forming a cylinder. The two halves may be separate components and coupled together using any suitable technique, or the two halves may be coupled together with a hinge, such as a living hinge. The housing 4030 is disposed around a portion of the inner shaft 4101. The housing 4030 comprises a clockwise internal female thread 4106 and an internal counterclockwise internal female thread 4107 disposed in an inside surface. The clockwise internal female thread 4106 and the counterclockwise female thread 4107 are configured to slideably receive the clockwise oriented male thread 4104 and the counterclockwise oriented male thread 4105 of the first nut 4102 and the second nut 4103, respectively. The ends of the housing 4030 are configured to couple with the flanges 4112 such that the housing 4030 is rotatable around the longitudinal axis of the inner shaft 4101. The end caps 4110 are configured to be disposed over the ends of the inner shaft 4101 such that the housing 4030 is retained in position around the inner shaft 4101.

In use, the steerable drainage device 4000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first and/or second direction by actuation of the tension control member 4050 such that the drainage tube 10 may be directed to the target location.

The housing 4030 of the tension control member 4050 may be grasped or held by the hand of the healthcare worker. Utilizing a suitable imaging system, such as x-ray, fluoroscopy, or ultrasound, a drainage tube 10 insertion direction may be determined. Adjustments to the insertion direction may be made by actuation of the tension control member 4050.

During use, counterclockwise rotation of the housing 4030 by the healthcare worker displaces the first nut 4102 proximally and the second nut 4103 distally such that tension is applied to the first wire 16 and tension is released from the second wire 17. The tension on the first wire 16 facilitates bending of the distal end 12 of the drainage tube 10 in a first direction $\alpha$. Clockwise rotation of the housing 4030 by the healthcare worker displaces the second nut 4103 proximally and the first nut 4102 distally such that tension is applied to the second wire 16 and tension is released from the first wire 16. The tension on the second wire 17 facilitates bending of the distal end 12 of the drainage tube 10 in a second direction $\beta$.

FIGS. 14-16C illustrate a steerable drainage device 5000 comprising the drainage tube 10 as previously described and a tension control member 5050 disposed adjacent the proximal end 11 of the drainage tube 10. The tension control member 5050 comprises a housing 5030, a knob 5121, and a locking member 5125.

The housing 5030 is configured to be grasped and held by the hand of a healthcare worker. The housing 5030 comprises an upper portion 5129, a lower portion 5130, and a cavity 5131. The upper and lower portions 5129, 5130 may be separate components and coupled together using any suitable technique, or they may be coupled together with a hinge, such as a living hinge. The cavity 5131 comprises a distal opening 5132 and a lower opening 5133. The drainage tube 10 may be partially disposed within the cavity 5131 such that a portion of the drainage tube 10 extends distally from the distal opening 5132 and a portion extends downwardly and proximally from the lower opening 5133.

In the illustrated embodiment, the housing 5030 further comprises the locking member 5125 comprising an arm 5128 and arm teeth 5126. The arm 5128 is disposed in the upper portion 5129 and extends proximally from a distal end of the upper portion 5129. The arm 5128 is configured in a cantilevered configuration such that the arm 5128 is configured to flex in a vertical plane. The arm teeth 5126 are disposed at a distal end of the arm 5128.

The knob 5121 comprises a handle 5122, a shaft 5123, and locking teeth 5124. The handle 5122 is disposed on the top portion of the knob 5121. The handle 5122 is configured to be grasped by the hand of the healthcare worker such that the knob 5121 may be rotated. For example, the handle 5122 may comprise an elongated vertical portion with a length substantially equivalent to the diameter of the upper portion of the knob 5121. The handle 5122 may comprise any suitable grip enhancing feature, such as bumps, dimples, surface texturing, elastomeric coating, etc.

The shaft 5123 extends downwardly from the upper portion of the knob 5121 into the cavity 5131. The shaft 5123 may be a cylinder. A plurality of locking teeth 5124 circumferentially surround an upper portion of the shaft 5123. The locking teeth 5124 are configured to selectively meshed with the arm teeth 5126 such that the locking teeth 5124 and the arm teeth 5126 rotationally lock the knob 5121. The first and second wires 16, 17 are coupled to the shaft 5123 in any suitable manner. For example, the first and second wires 16, 17 may be coupled to the shaft 5123 utilizing a fastener, such as a screw, glue, etc. The first wire 16 may be wrapped around the shaft 5123 in a first direction, and the second wire 17 may be wrapped around the shaft 5123 in a second direction. The shaft 5123 may be rotatably coupled to the lower portion 5130 of the housing 5030 in any suitable manner, such as a screw.

In use, the steerable drainage device 5000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first and/or second direction by actuation of the tension control member 5050 such that the drainage tube 10 may be directed to the target location.

The housing 5030 of the tension control member 5050 is grasped or held by the hand of the healthcare worker. Utilizing a suitable imaging system, such as x-ray, fluoroscopy, or ultrasound, a drainage tube 10 insertion direction may be determined. Adjustments to the insertion direction may be made by actuation of the tension control member 5050.

During use, the handle 5122 is grasped by the hand of the healthcare worker. Depression of the locking member 5125 unmeshes the arm teeth 5126 and the locking teeth 5124 such that the knob 5121 is rotatable. Rotation of the handle 5122 in a first direction γ by the healthcare worker rotates the shaft 5123 in the first direction γ. As the shaft 5123 is rotated in the first direction γ, the first wire 16 is wrapped around the shaft 5123 such that tension may be applied to the first wire 16. The tension on the first wire 16 facilitates bending of the distal end 12 of the drainage tube 10 in a first direction α. Rotation of the handle 5122 by the healthcare worker in the second direction Δ rotates the shaft 5123 in the second direction Δ. As the shaft 5123 is rotated in the second direction Δ, the second wire 17 is wrapped around the shaft 5123 such that tension may be applied to the second wire 17. The tension on the second wire 17 facilitates bending of the distal end 12 of the drainage tube 10 in a second direction β. Release of the locking member 5125 meshes the arm teeth 5126 and the locking teeth 5124 such that the knob 5121 is rotatably locked and the distal end 12 of the drainage tube 10 is maintained in an arcuate configuration.

FIGS. 17-19C illustrate a steerable drainage device 6000 comprising the drainage tube 10 as previously described and a tension control member 6050 disposed adjacent the proximal end 11 of the drainage tube 10. The tension control member 6050 comprises a housing 6030 and a knob 6140.

The housing 6030 is configured to be grasped and held by the hand of a healthcare worker. The housing 6030 comprises a first portion 6147, a second portion 6148, and a cavity 6149. The first and second portions 6147, 6148 may be separate components and coupled together using any suitable technique, or they may be coupled together with a hinge, such as a living hinge. The cavity 6149 comprises a distal opening 6150, a proximal opening 6151 in axial alignment with the distal opening 6150, and a knob opening 6152. The drainage tube 10 may be partially disposed within the cavity 6149 such that a portion of the drainage tube 10 extends distally from the distal opening 6150 and a portion extends proximally from the proximal opening 6151.

In the illustrated embodiment, the housing 6030 further comprises a first rod 6144 and a second rod 6145. The first rod 6144 is disposed within the first portion 6147 of the housing 6030 such that a portion of the first rod 6144 is disposed within the cavity 6149 and opposing ends are disposed external to the cavity 6149. The second rod 6145 is disposed within the second portion 6148 of the housing 6030 such that a portion of the second rod 6145 is disposed within the cavity 6149 and opposing ends are disposed external to the cavity 6149. The first and second rods 6144, 6145 are positioned with a tilted orientation such that lower ends of the first and second rods 6144, 6145 are closer to a central, longitudinal axis of the housing 6030 than the upper ends.

The knob 6140 comprises a handle 6141, a disk 6142, and a wire tensioning block 6143. The handle 6141 is disposed on the top portion of the knob 6140. The handle 6141 is configured to be grasped by the hand of the healthcare worker such that the knob 6140 may be rotated. For example, the handle 6141 may comprise an elongated vertical portion with a length substantially equivalent to the diameter of the upper portion of the knob 6140. The handle 6141 may comprise any suitable grip enhancing feature, such as bumps, dimples, surface texturing, elastomeric coating, etc.

The disk 6142 extends downwardly from the upper portion of the knob 6140 into the cavity 6149 through the knob opening 6152. The disk 6142 has a circular shape. The disk 6142 comprises a ring 6155 configured to be disposed in a circular channel 6154 of the housing 6030. A plurality of detents 6146 circumferentially surround a perimeter of the disk 6142. The detents 6146 are configured to frictionally engage a wall of the knob opening 6152 such that the knob 6140 is rotationally locked.

The wire tensioning block 6143 extends downwardly from the disk 6142. The block 6143 is disposed toward the perimeter of the disk 6142 such that the block 6143 is offset from a center point of the disk 6142. The first and second wires 16, 17 may be coupled to a peripheral portion of the block 6143 in any suitable manner. The first wire 16 is coupled to the block 6143 such that the wire 16 extends from the block 6143 toward the first rod 6144 and around the portion of the first rod 6144 disposed within the cavity 6149. The second wire 17 is coupled to the block 6143 such that the second wire 17 extends from the block 6143 toward the second rod 6145 and around the portion of the second rod 6145 disposed within the cavity 6149.

In use, the steerable drainage device 6000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first α and second β directions by actuation of the tension control member 6050 such that the drainage tube 10 may be directed to the target location.

The housing 6030 of the tension control member 6050 may be grasped or held by the hand of the healthcare worker. Utilizing a suitable imaging system, such as x-ray, fluoroscopy, or ultrasound, a drainage tube 10 insertion direction may be determined. Adjustments to the direction the distal end 12 of the drainage tube 10 is pointed may be made by actuation of the tension control member 6050.

During use, the handle 6141 is grasped by the hand of the healthcare worker. Rotation of the handle 6141 in a first direction by the healthcare worker with enough rotational force to overcome the frictional force of the detents 6146 against the housing 6030 rotates the disk 6142 in the first direction γ. As the disk 6142 is rotated in the first direction γ, the first wire 16 is pulled by the block 6143 around the first rod 6144 such that tension is applied to the first wire 16. The tension on the first wire 16 facilitates bending of the distal end 12 of the drainage tube 10 in a first direction α. Rotation of the handle 6141 by the healthcare worker in the second direction Δ rotates the disk 6142 in the second direction Δ. As the disk 6142 is rotated in the second direction Δ, the second wire 17 is pulled by the block 6143 around the second rod 6145 such that tension is applied to the second wire 17. The tension on the second wire 17 facilitates bending of the distal end 12 of the drainage tube 10 in a second direction β.

FIGS. 20-22C illustrate a steerable drainage device 7000 comprising the drainage tube 10 as previously described and a tension control member 7050 disposed adjacent the proximal end 11 of the drainage tube 10. The tension control member 7050 comprises a housing 7030 and a knob 7130.

The housing 7030 is configured to be grasped and held by the hand of a healthcare worker. The housing 7030 comprises an upper portion 7169, a lower portion 7170, and a cavity 7171. The upper and lower portions 7169, 7170 may be separate components and coupled together using any suitable technique, or they may be coupled together with a hinge, such as a living hinge. The cavity 7171 comprises a distal opening 7172, a lower opening 7173, and a knob opening 7174. The drainage tube 10 may be partially disposed within the cavity 7171 such that a portion of the drainage tube 10 extends distally from the distal opening 7172 and a portion extends downwardly and proximally from the lower opening 7173.

In the illustrated embodiment, the knob 7160 comprises a handle 7161, a disk 7162, a shaft 7164, and a locking teeth ring 7165. The handle 7161 is disposed on a top surface of the disk 7162. The handle 7161 is configured to be grasped by the hand of the healthcare worker such that the knob 7160 may be rotated. For example, the handle 7161 may comprise an elongated vertical portion with a length less than a diameter of the disk 7162 and less than a diameter of the knob opening 7174. The handle 7161 is disposed through the knob opening 7174 such that the handle 7161 may be grasped by the healthcare worker. The handle 7161 may comprise any suitable grip enhancing feature, such as bumps, dimples, surface texturing, elastomeric coating, etc.

Figure 21:
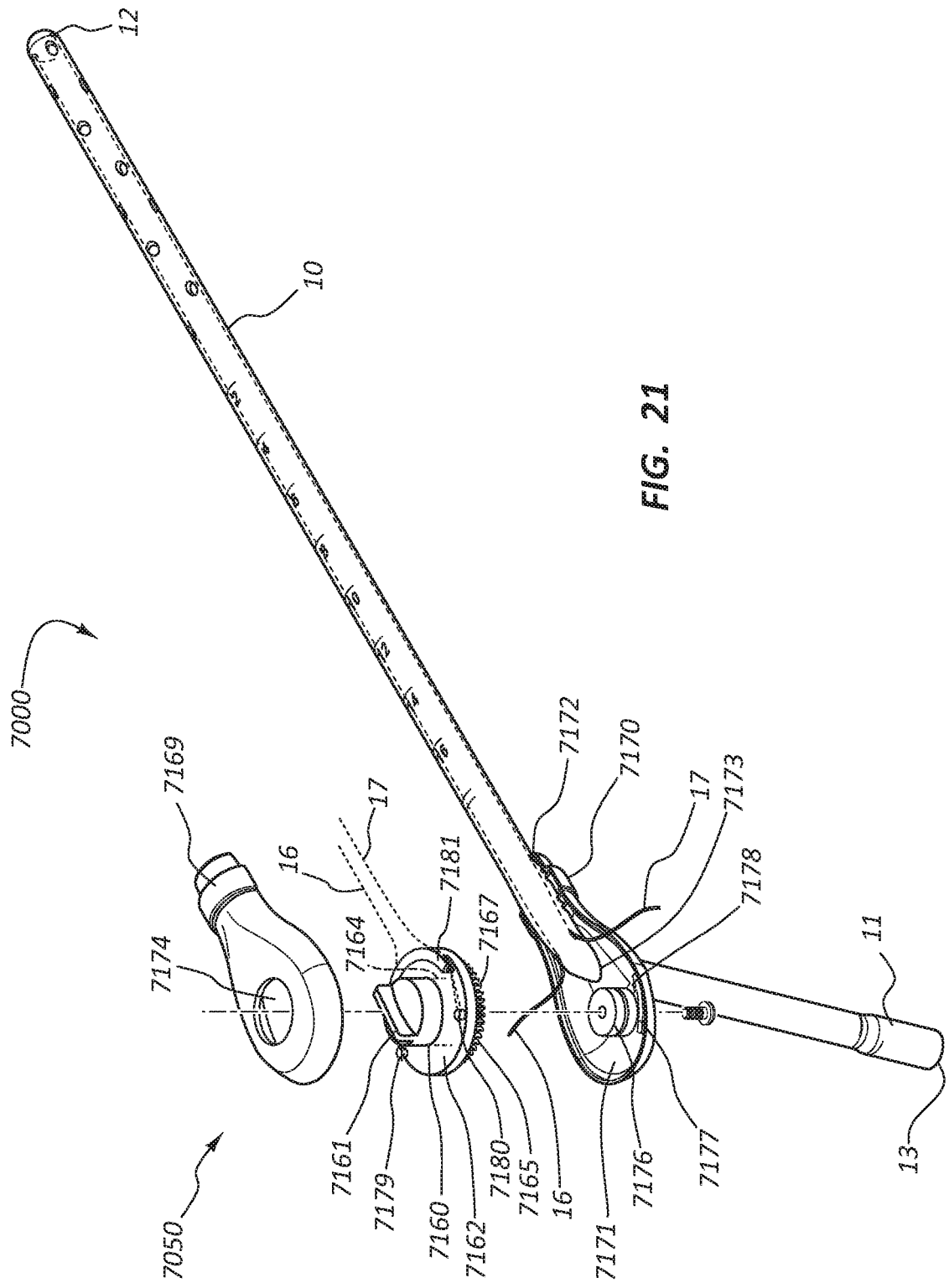
FIG. 21 is a perspective, exploded, view of the steerable drainage device of FIG. 20.
Figure 22A:
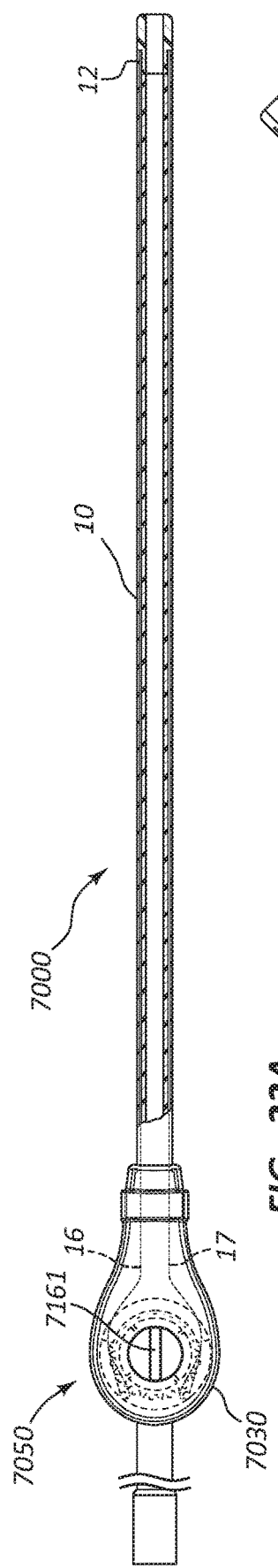
FIG. 22A is a top partial cross-sectional view of the steerable drainage device of FIG. 20 in a straight configuration.
Figure 22B:
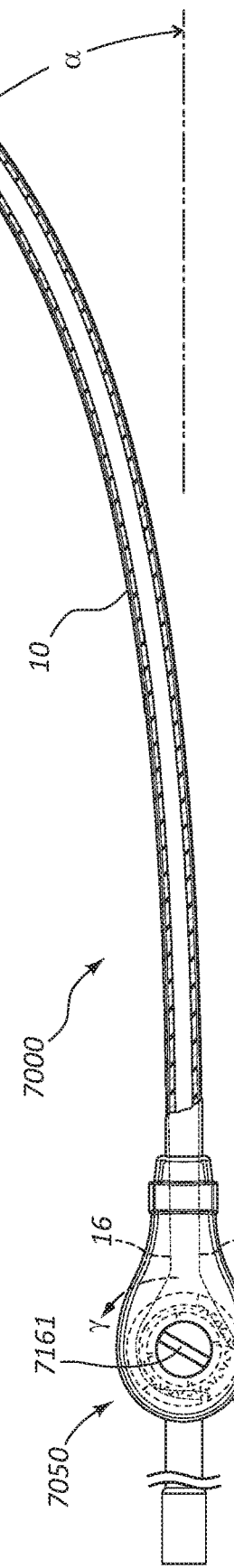
FIG. 22B is a top partial cross-sectional view of the steerable drainage device of FIG. 20, where the device is bent in a first direction.
Figure 22C:
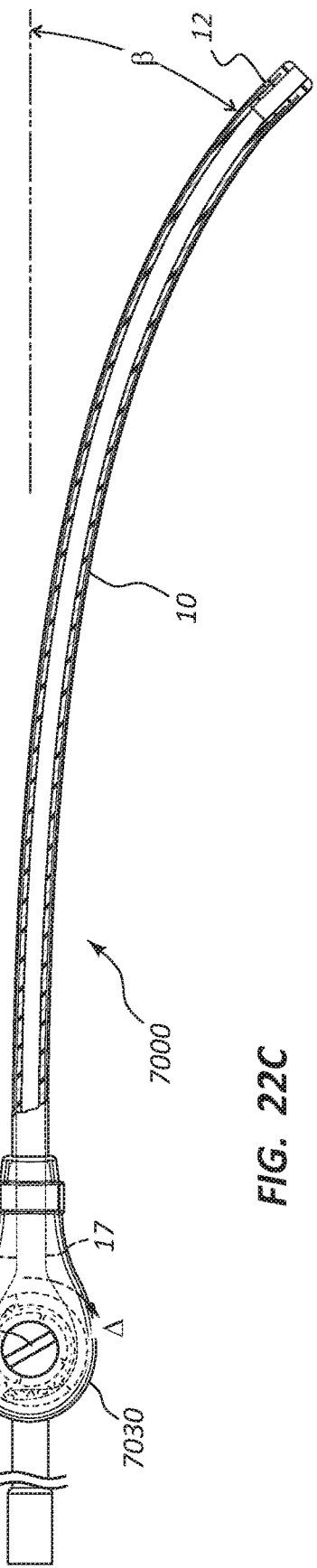
FIG. 22C is a top partial cross-sectional view of the steerable drainage device of FIG. 20, where the device is bent in a second direction.
Figure 23:
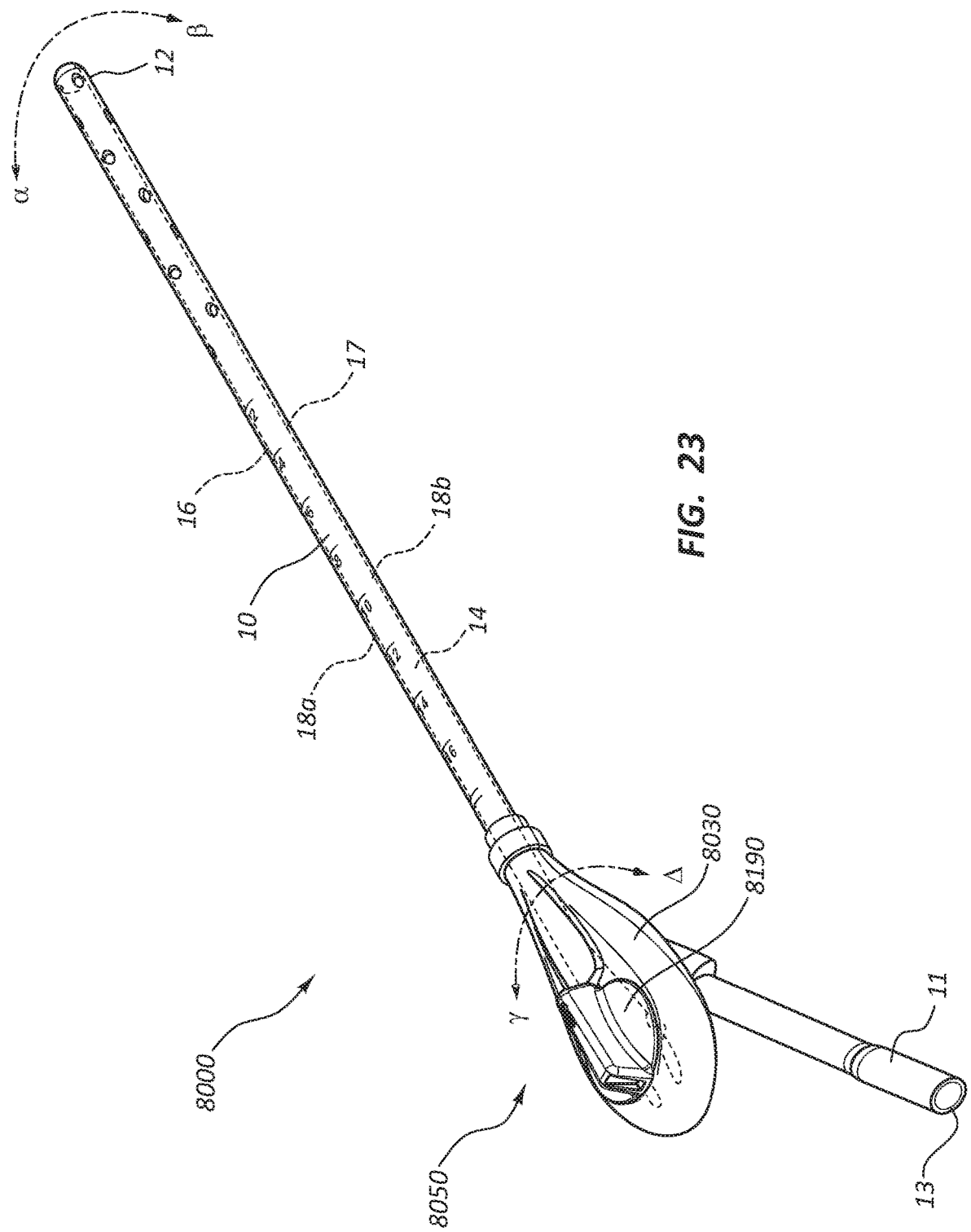
FIG. 23 is a perspective view of a steerable drainage device.

The first and second wires 16, 17 are coupled to the disk 7162 in any suitable manner. For example, as shown in FIG. 21, the disk 7162 comprises a first hook 7179 and a second hook 7180 disposed on the upper surface of the disk 7162 and adjacent a periphery of the disk 7162. The first wire 16 may comprise a looped end. The looped end is disposed over the first hook 7179 such that the first wire 16 is coupled to the disk 7162. Similarly, the second wire 17 may comprise a looped end and the looped end is disposed over the second hook 7180 such that the second wire 17 is coupled to the disk 7162. The disk 7162 may further comprise an arcuate shaped hood 7181 disposed on the upper surface and adjacent the periphery of the disk 7162. The hood 7181 may extend around a portion of the periphery of the disk 7162. The hood 7181 is configured to provide a feature for wrapping of the first and second wires 16, 17 when the knob 7160 is rotated.

The teeth ring 7165 extends from a bottom surface of the disk 7162. The locking teeth ring 7165 comprises a plurality of radially outwardly directed teeth 7167. The diameter of the locking teeth ring 7165 may be less than the diameter of the disk 7162. The shaft 7164 extends from the bottom surface of the disk 7162. The shaft 7164 may be a cylinder sized to couple with a rotation support 7176 disposed on an inner surface of the lower portion 7170 of the housing 7030. The lower surface of the disk 7162 may be supported by a vertical wall 7177 disposed on the inner surface of the lower portion 7170. The vertical wall 7177 is configured with an arcuate shape. The vertical wall 7177 comprises at least one locking tooth 7178 extending radially inward. The locking tooth 7178 is configured to mesh with the teeth 7167 of the locking teeth ring 7165 such that the knob 7160 can be rotationally locked. The knob 7160 is rotatably coupled to the lower housing 170 using any suitable coupling device, such as a screw, a flat head pin, etc.

In use, the steerable drainage device 7000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first and/or second direction by actuation of the tension control member 7050 such that the drainage tube 10 may be directed to the target location.

The housing 7030 of the tension control member 7050 is grasped or held by the hand of the healthcare worker. Utilizing a suitable imaging system, such as x-ray, fluoroscopy, or ultrasound, a drainage tube 10 insertion direction may be determined. Adjustments to the direction the distal end 12 of the drainage tube 10 is pointed may be made by actuation of the tension control member 7050.

During use, the handle 7161 is grasped by the hand of the healthcare worker. Rotation of the handle 7161 in a first direction by the healthcare worker with adequate rotational force to unmesh the locking tooth 7178 and the teeth 7127 of the locking ring 7165 rotates the disk 7162 in the first direction γ. As the disk 7162 is rotated in the first direction γ, the first wire 16 is wrapped around the hood 7181 such that tension is applied to the first wire 16. The tension on the first wire 16 facilitates bending of the distal end 12 of the drainage tube 10 in a first direction α. Rotation of the handle 7161 by the healthcare worker in the second direction Δ rotates the disk 7162 in the second direction Δ. As the disk 7162 is rotated in the second direction Δ, the second wire 17 is wrapped around the hood 7181 such that tension may be applied to the second wire 17. The tension on the second wire 17 facilitates bending of the distal end 12 of the drainage tube 10 in a second direction β.

FIGS. 23-25C illustrate a steerable drainage device 8000 comprising the drainage tube 10 as previously described and a tension control member 8050 disposed adjacent the proximal end 11 of the drainage tube 10. The tension control member 8050 comprises a housing 8030, a knob 8190, a first disk 8195, a second disk 8198, and a locking member 8201.

The housing 8030 is configured to be grasped and held by the hand of a healthcare worker. The housing 8030 comprises an upper housing 8203, a lower housing 8204, and a cavity 8205. The upper and lower housings 8023, 8024 may be separate components and coupled together using any suitable technique, or they may be coupled together with a hinge, such as a living hinge. The cavity 8025 comprises a distal opening 8206, a lower opening 8207, and a knob opening 8208. The drainage tube 10 may be partially disposed within the cavity 8205 such that a portion of the drainage tube 10 extends distally from the distal opening 8206 and a portion extends downwardly and proximally from the lower opening 8207.

In the illustrated embodiment, the knob 8190 comprises a handle 8191, a locking teeth ring 8192, and a shaft 8194. The handle 8191 is disposed on a top surface of the locking teeth ring 8192. The handle 8191 is configured to be grasped by the hand of the healthcare worker such that the knob 8190 may be rotated. For example, the handle 8191 may comprise an elongated vertical portion with a length greater than a diameter of the locking teeth ring 8192. The handle 8191 is disposed through the knob opening 8208 such that the handle 8191 is graspable by the healthcare worker. The handle 8191 may comprise any suitable grip enhancing feature, such as bumps, dimples, surface texturing, elastomeric coating, etc.

The locking teeth ring 8192 is disposed below the handle 8191. The locking teeth ring 8192 comprises a plurality of radially outwardly directed teeth 8193. The shaft 8194 extends downward from the locking teeth ring 8192. The shaft 8194 may be generally cylindrical in shape with a key tab 8210 extending radially outward from the shaft 8194. The shaft 8194 is coupled to the lower housing 8204 using any suitable fastener, such as a screw, flathead pin, etc., into a lower end of the shaft 8194.

The first disk 8195 is disposed within the cavity 8205. The first disk 8195 comprises a first groove 8196 disposed about a perimeter and configured to receive the first wire 16 such that the first wire 16 can be wrapped around the first disk 8195. The first disk 8195 further comprises a first central passage 8197 configured in the shape of a truncated circle. The second disk 8198 is disposed within the cavity 8205 below the first disk 8195. The second disk 8198 comprises a second groove 8199 disposed about a perimeter and configured to receive the second wire 17 such that the second wire 17 can be wrapped around the second disk 8198 in a second direction. The second disk 8198 further comprises a second central passage 8200 configured in the shape of a truncated circle. The diameter of the first and second disks 8195, 8198 is less than the diameter of the locking teeth ring 8192. An arcuate shaped retention wall 8213 extends upwardly from an inner surface of the lower housing 8204. The retention wall 8213 is configured to retain the first and second disks 8195, 8198 in vertical alignment.

Figure 24:
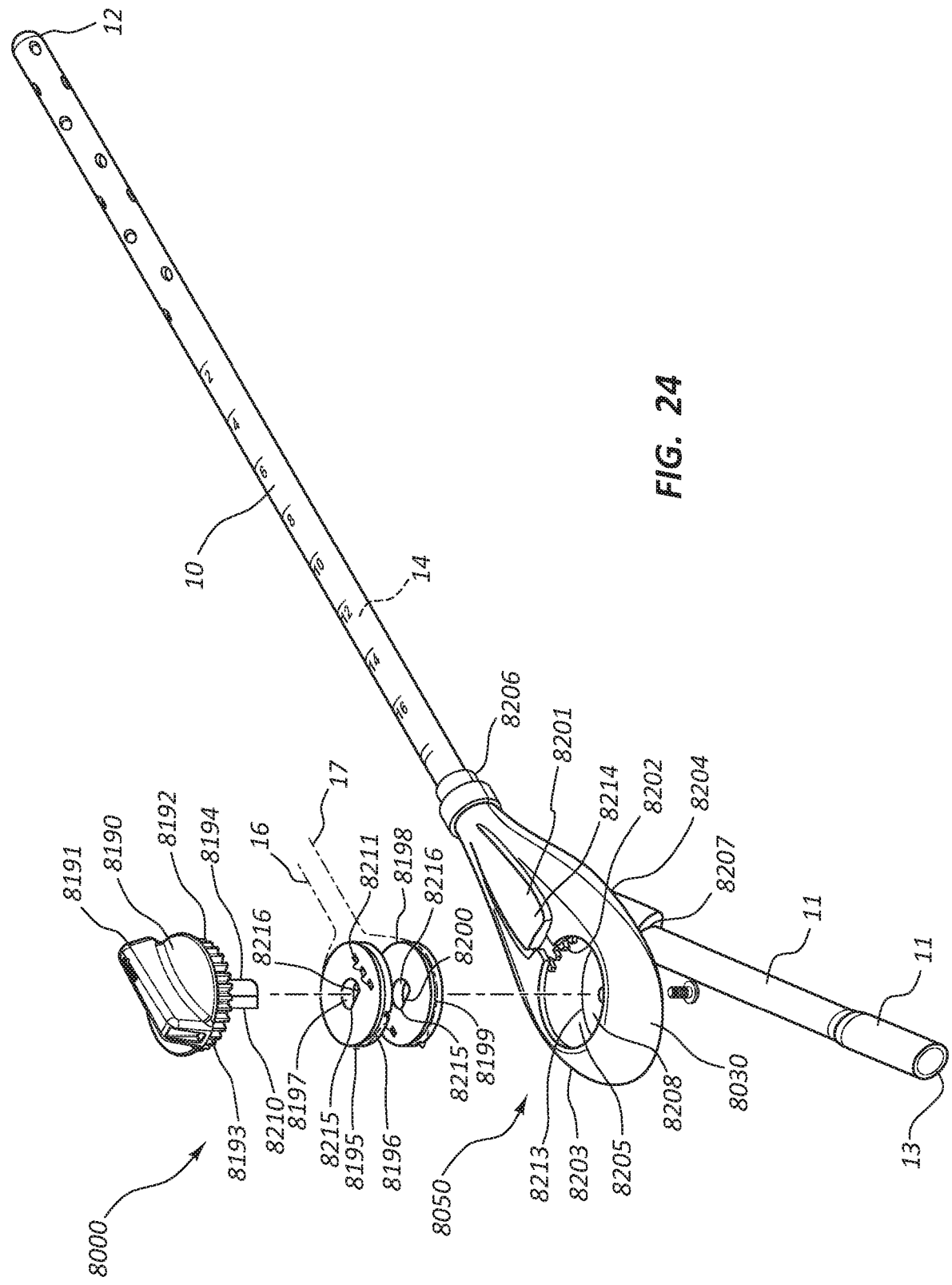
FIG. 24 is a perspective, exploded, view of the steerable drainage device of FIG. 23.
Figure 25A:
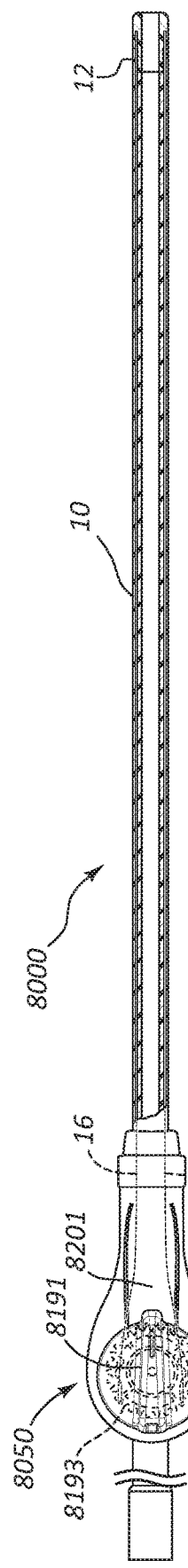
FIG. 25A is a top partial cross-sectional view of the steerable drainage device of FIG. 23 in a straight configuration.
Figure 25B:
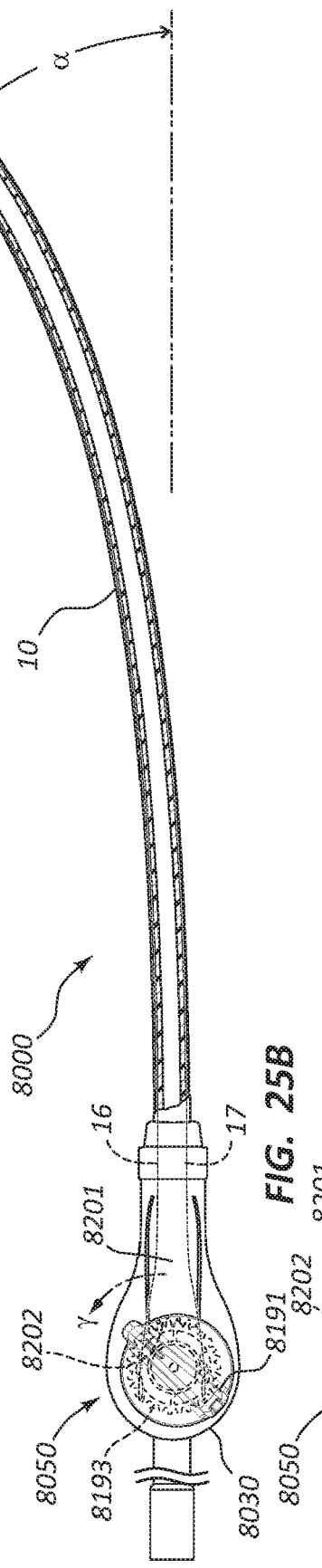
FIG. 25B is a top partial cross-sectional view of the steerable drainage device of FIG. 23, where the device is bent in a first direction.
Figure 25C:
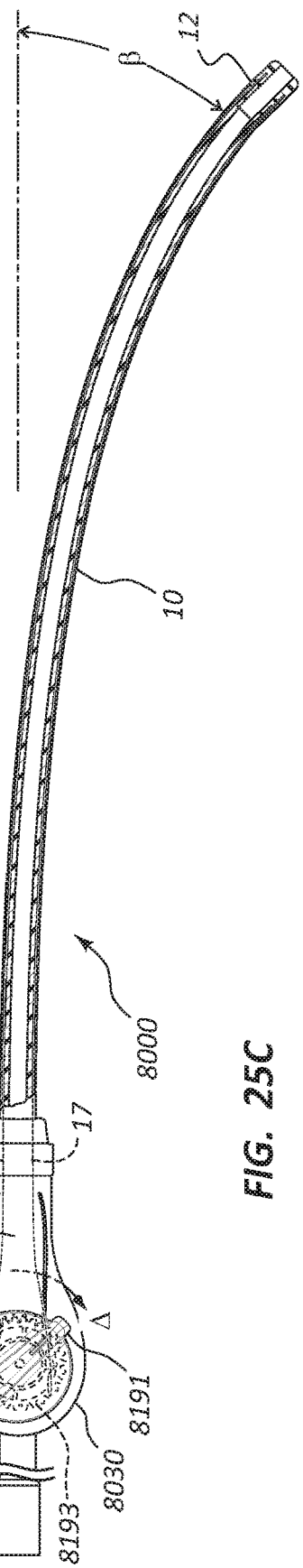
FIG. 25C is a top partial cross-sectional view of the steerable drainage device of FIG. 23, where the device is bent in a second direction.
Figure 26:
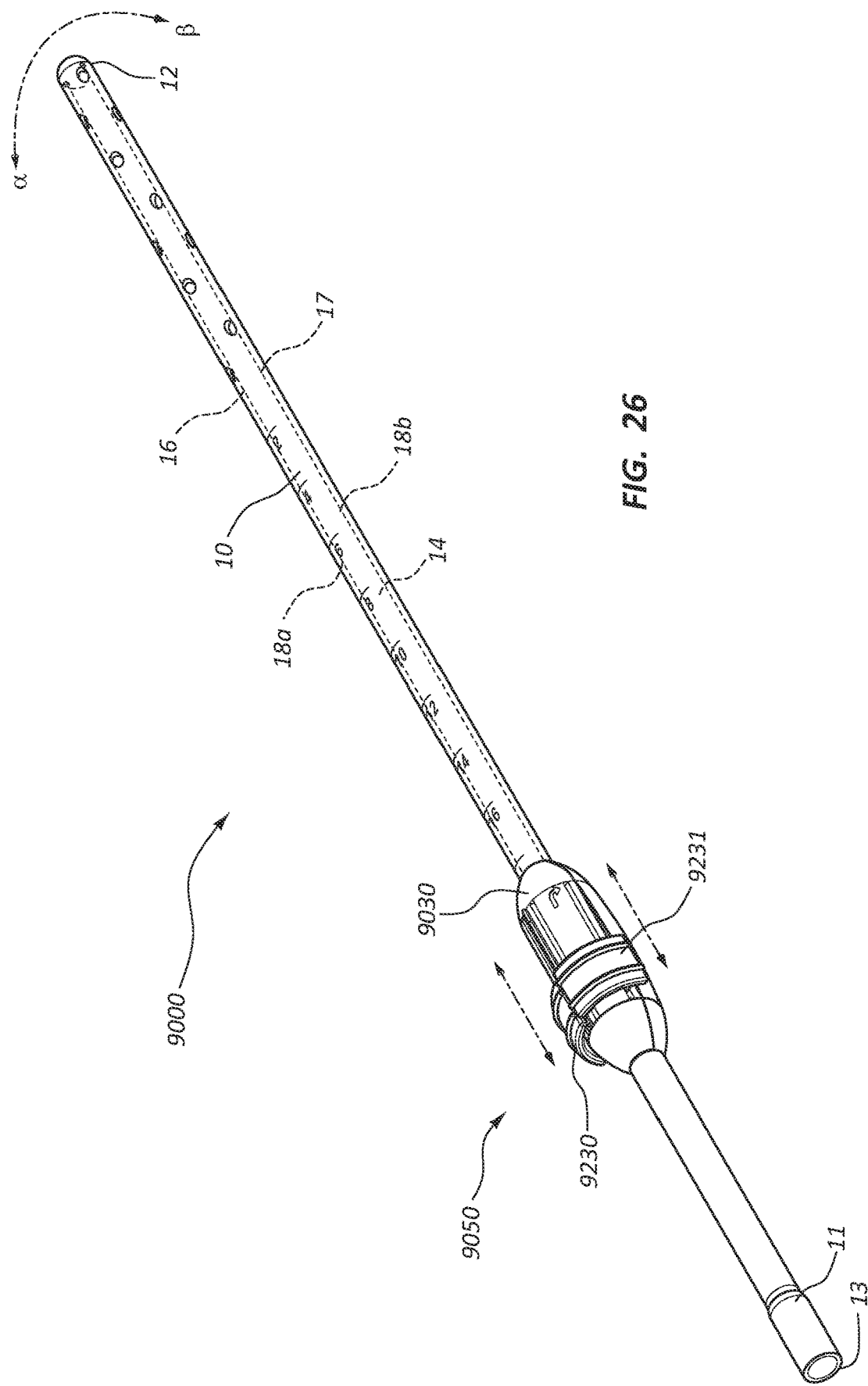
FIG. 26 is a perspective view of a steerable drainage device.
Figure 28A:
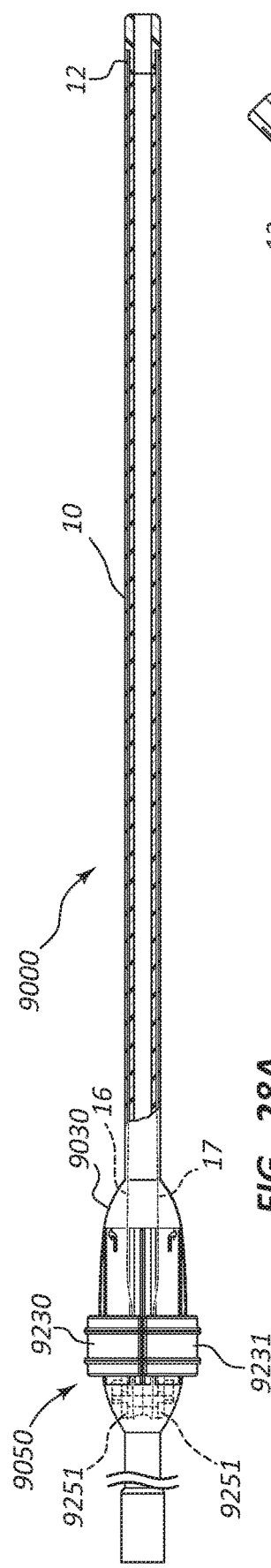
FIG. 28A is a top partial cross-sectional view of the steerable drainage device of FIG. 26 in a straight configuration.
Figure 28B:
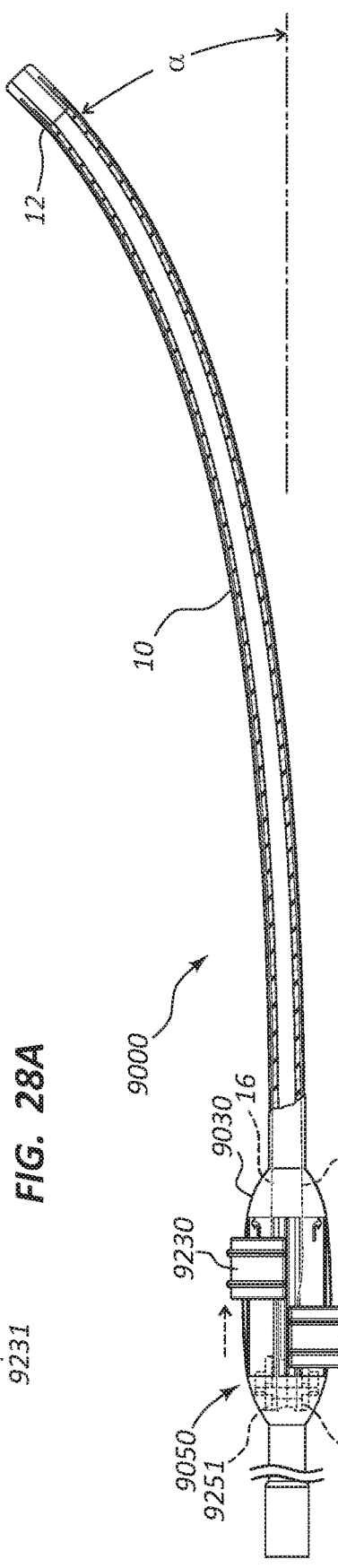
FIG. 28B is a top partial cross-sectional view of the steerable drainage device of FIG. 26, where the device is bent in a first direction.
Figure 28C:
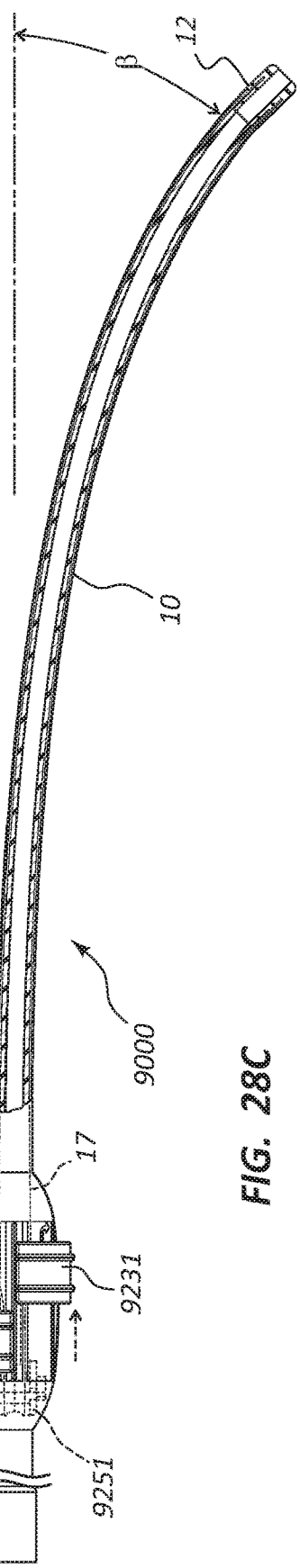
FIG. 28C is a top partial cross-sectional view of the steerable drainage device of FIG. 26, where the device is bent in a second direction.

The first and second wires 16, 17 may be coupled to the first and second disks 8195, 8198, respectively, in any suitable manner. For example, as shown in FIG. 24, the first and second wires 16, 17 are coupled to the first and second disks 8195, 8198, respectively, utilizing a plurality of stays 8211.

The locking member 8201 is a cantilevered portion of the upper housing 8203. The locking member 8201 comprises a button 8214 and locking teeth 8202. The locking teeth 8202 are disposed at the proximal end of the locking member 8201 such that the locking teeth 8202 are configured to mesh with teeth 8193 of the locking teeth ring 8192 when the tension control member 8050 is in a locked configuration. The button 8214 is disposed adjacent a proximal end of the locking member 8201 and extends upward above an outer surface of the upper housing 8203. The button 8214 is configured to be depressed by a finger of the healthcare worker such that the locking teeth 8202 unmesh from the teeth 8193 of the locking ring 8192 to allow rotation of the knob 8190.

In use, the steerable drainage device 8000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in first α and second β directions by actuation of the tension control member 8050 such that the drainage tube 10 may be directed to the target location.

The housing 8030 of the tension control member 8050 is grasped or held by the hand of the healthcare worker. Utilizing a suitable imaging system, such as x-ray, fluoroscopy, or ultrasound, a drainage tube insertion direction may be determined. Adjustments to the direction the distal end 12 of the drainage tube 10 is pointed may be made by actuation of the tension control member 8050.

During use, the button 8214 of the locking member 8201 is depressed by the finger of the healthcare worker such that the locking teeth 8202 of the locking member 8201 unmesh from the teeth 8193 of the locking ring 8192, allowing the knob 8190 to be rotated in the first or second direction. The handle 8191 is grasped by the hand of the healthcare worker. Rotation of the handle 8191 in the first direction γ rotates the first disk 8195 and the second disk 8198 in the first direction γ. The key tab 8210 of the shaft 8194 engages the first truncated portions 8215 of the first central passage 8197 and the second central passage 8200 such that the first and second disks 8195, 8198 rotate in the first direction γ. As the first disk 8195 is rotated in the first direction γ, the first wire 16 is wrapped around the periphery in the first groove 8196 such that tension is applied to the first wire 16 and the distal end 12 of the drainage tube 10 is bent in a first direction α. As the second disk 8198 is rotated in the first direction γ the second wire 17 is displaced from the second groove 8199 and pulled distally by bending of the drainage tube 10 in the first direction α. Rotation of the handle 8191 in the second direction Δ rotates the first disk 8195 and the second disk 8198 in the second direction Δ. The key tab 8210 of the shaft 8194 engages the second truncated portions 8216 of the first central passage 8197 and the second central passage 8200 such that the first and second disks 8195, 8198 rotate in the second direction Δ. As the second disk 8198 is rotated in the second direction Δ, the second wire 17 is wrapped around the periphery in the second groove 8199 such that tension is applied to the second wire 17. The tension on the second wire 17 facilitates bending of the distal end 12 of the drainage tube 10 in the second direction β. As the first disk 8195 is rotated in the second direction the first wire 16 is displaced from the first groove 8196 and pulled distally by bending of the drainage tube 10 in the second direction.

FIGS. 26-28C illustrate a steerable drainage device 9000 comprising the drainage tube 10 as previously described and a tension control member 9050 disposed adjacent the proximal end 11 of the drainage tube 10. The tension control member 9050 comprises a housing 9030, a first button 9230, a second button 9231, and a pulley 9232.

The housing 9030 is configured to be grasped and held by the hand of a healthcare worker. The housing 9030 may be generally cylindrical in shape and comprise an upper housing 9235, a lower housing 9236, and a central passage 9245. The upper and lower housings 9235, 9236 may be separate components and coupled together using any suitable technique, such as a snap fit, welding, gluing, etc., or they may be coupled together with a hinge, such as a living hinge. The central passage 9245 comprises a distal opening 9249 and a proximal opening 9250. The central passage 9245 is sized such that the drainage tube 10 may be partially disposed within the central passage 9245. A portion of the drainage tube 10 may extend distally from the distal opening 9249 and a portion may extend proximally from the proximal opening 9250.

In the illustrated embodiment, the lower housing 9236 further comprises a rear shroud 9237 disposed over the drainage tube 10 at a proximal end of the lower housing 9236. The rear shroud 9237 may be generally conical in shape. The rear shroud 9237 may be coupled to a distal end of the upper housing 9235 and the lower housing 9236 using any suitable technique, such as snap fit, welding, gluing, etc.

The upper housing 9235 comprises two button channels 9239. The button channels 9239 are disposed on an exterior surface on lateral sides of the upper housing 9235. The button channels 9239 extend over a length of the upper housing 9235 and are L-shaped. The button channels 9239 are disposed substantially parallel to one another. In other embodiments, the upper housing 9235 may comprise more than two button channels 9239. For example, as illustrated in FIG. 27, the upper housing 9235 comprises four button channels 9239 with two button channels 9239 disposed on each lateral half of the upper housing 9235. The upper housing 9235 may be configured as an integral component. In some embodiments, the upper housing 9235 may comprise two lateral halves.

The first button 9230 and the second button 9231 are configured to be slidingly coupled to the upper housing 9235. The buttons 9230, 9231 comprise L-shaped rails 9240 disposed on an inside surface of the buttons 9230, 9231 and extending longitudinally over a length of the buttons 9230, 9231. The L-shaped rails 9240 are configured to be disposed into the button channels 9239 such that the L-shaped rails 9240 slide longitudinally within the button channels 9239 and are prevented from being radially displaced from the button channels 9239. The buttons 9230, 9231 comprise at least one L-shaped rail 9240. In other embodiments, the buttons 9230 comprise two or more L-shaped rails 9240. The buttons 9230, 9231 may further comprise grip enhancing features on a top surface, such as ribs, bumps, detents, roughened surface, elastomeric coating, etc. The first wire 16 is fixedly coupled to the first button 9230, and the second wire 17 is fixedly coupled to the second button 9231.

The pulley 9232 comprises a central cylinder 9251, a first wire channel 9233, a second wire channel 9234, and support posts 9238. The pulley 9232 is disposed adjacent the proximal end of the housing 9030 and configured to be a non-rotating pulley. The pulley 9232 may of unitary construction. In other embodiments, the pulley 9232 may comprise lateral half portions. The central cylinder 9251 comprises a tube passage 9252 extending across a central portion of the central cylinder 9251. The tube passage 9252 is sized such that the drainage tube 10 can be disposed within the passage 9252 with portions extending distally and proximally. The central cylinder 9251 is shown to further comprise a notch 9241 and a shoulder 9242 configured to abut portions of the upper housing 9235 such that the pulley 9232 is prevented from distal displacement and rotation.

The first and second wire channels 9233, 9234 are disposed in an exterior surface of the central cylinder 9251 such that the first wire channel 9233 is adjacent a lateral end of the central cylinder 9251 and the second wire channel 9234 is adjacent an opposing lateral end of the central cylinder 9251. The wire channels 9233, 9234 extend about a circumference of the central cylinder 9251. The first wire channel 9233 is configured to receive the first wire 16 and the second wire channel 9234 is configured to receive the second wire 17 such that the first and second wires 16, 17 wrap around at least a portion of the pulley 9232 from a lower portion of the pulley 9232 to an upper portion of the pulley 9232.

The support posts 9238 extend laterally from each end of the central cylinder 9251. The support posts 9238 are disposed within recesses of the housing 9030. The support posts 9238 comprise a post notch 9243 and a post shoulder 9244 configured to abut with a portion of the housing such that the pulley 9232 is prevented from distal displacement and rotation.

In use, the steerable drainage device 9000 may be utilized to insert the drainage tube 10 into a body cavity, such as the pleural cavity to drain fluid from around the lungs, and direct the tip of the drainage tube 10 to a targeted location within the body cavity. The drainage tube 10 may be inserted into the body cavity utilizing any suitable technique, such as through a thoracotomy or through an introducer. The distal end 12 of the drainage tube 10 may be bent in the first $\alpha$ and second $\beta$ directions by actuation of the tension control member 9050 such that the drainage tube 10 may be directed to the target location.

The housing 9030 of the tension control member 9050 is grasped or held by the hand of the healthcare worker. Utilizing a suitable imaging system, such as x-ray, fluoroscopy, or ultrasound, a drainage tube insertion direction may be determined. Adjustments to the direction the distal end 12 of the drainage tube 10 is pointed may be made by actuation of the tension control member 9050.

The first button 9230 is displaced distally by the finger of the healthcare worker. As the first button 9230 is displaced distally, tension is applied to the first wire 16 such that the first wire 16 is pulled around the pulley 9232 within the first wire channel 9233 and the distal end 12 of the drainage tube 10 is bent in a first direction $\alpha$. As the drainage tube 10 bends in the first direction $\alpha$, the second wire 17 is displaced distally through the second wire channel 9234 and the second button 9231 is displaced proximally. The second button 9231 is displaced distally relative to the housing 9030 to bend the distal end 12 of the drainage tube 10 in a second direction $\beta$. As the second button 9231 is displaced distally, tension is applied to the second wire 17 such that the second wire 17 is pulled around the pulley 9232 within the second wire channel 9234 and the distal end 12 of the drainage tube 10 is bent in the second direction $\beta$. As the drainage tube 10 bends in the second direction, the first wire 16 is displaced distally through the first wire channel 9233 and the first button 9230 is displaced proximally.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A steerable elongated medical device, comprising:
a housing having an opening at a proximal end region of the housing, an opening at a distal end region of the housing opposite the proximal end region, and a longitudinal passage extending through the housing between the opening at the proximal end region and the opening at the distal end region;
a tube configured to be inserted into a patient's body and extending through the longitudinal passage such that the housing is positioned between a proximal end of the tube and a distal end of the tube;
first and second wires slidably extending longitudinally through a wall of the tube and attached adjacent the distal end of the tube; and
a tension control member disposed at least partially in the passage between the opening at the proximal end region of the housing and the opening at the distal end region of the housing, wherein the tension control member is configured to selectively apply a tension force to the first and second wires to bend the tube,
wherein the tension control member comprises a rack and pinion linear displacement mechanism comprising:
a first rack operatively coupled to the first wire;
a second rack operatively coupled to the second wire;
a gear secured in a position within the longitudinal passage and configured to mesh with the first and second racks;
a button coupled to the first rack and configured to displace the first rack proximally and distally; and
a biasing member disposed between the button and the first rack that actively locks the button into a locked configuration,
wherein the button transitions to an unlocked configuration when the button is decompressed, in the unlocked configuration, the button is slidable in a proximal direction and a distal direction,
wherein at least one of the first rack or the second rack includes a slot extending longitudinally thereon and at least one of the first wire or the second wire is looped through the slot to operably couple thereto.

2. The medical device of claim 1, wherein the button is configured to lock the tension control member such that the tube is in a bent configuration.

3. The medical device of claim 1, wherein the tension control member is configured to be activated by only one hand of a healthcare worker.

4. The medical device of claim 1, wherein the tension control member is configured to selectively displace the first and second wires proximally.

5. The medical device of claim 1, wherein the tension control member is configured to bend the tube into an arcuate shape of up to 180 degrees in a single plane.

6. The medical device of claim 1, wherein the at least one of the first rack or the second rack including the slot extending longitudinally thereon and at least one of the first wire or the second wire being looped through the slot to operably couple thereto includes:
the first rack includes a first slot extending longitudinally along at least a portion of the first rack, the first wire being looped through the first slot effective to couple the first wire to the first rack; and
the second rack includes a second slot extending longitudinally along at least a portion of the second rack, the second wire being looped through the second slot effective to couple the second wire to the second rack.

7. The medical device of claim 1, further comprising two opposing openings on the tube between the tension control member and the distal end of the tube, wherein the first wire and the second wire extend from the tension control member, at least partially into the tube, to the distal end of the tube.

8. A method of inserting a medical device into a patient's body, comprising:
obtaining a steerable medical device comprising:
a housing having an opening at a proximal end region of the housing, an opening at a distal end region of the housing, and a longitudinal passage extending through the housing between the opening at the proximal end region and the opening at the distal end region;
an elongate tube extending through the longitudinal passage such that the housing is positioned between a proximal end of the tube and a distal end of the tube;
first and second wires; and
a steering member disposed at least partially in the passage between the opening and the proximal end region of the housing and the opening at the distal end region of the housing, the steering member including a first rack and a second rack being coupled to the first and second wires, respectively, wherein at least one of the first rack or the second rack includes a slot extending longitudinally thereon and at least one of the first wire or the second wire is looped through the slot to operably couple thereto;
inserting the distal end of the elongate tube into the patient's body;
actuating the steering member by depressing a button and sliding the button proximally or distally, wherein tension is selectively applied to the first and second wires to bend the distal end of the elongate tube; and
directing the distal end to a target location.

9. The method of claim 8, further comprising disengaging a locking member.

10. The method of claim 8, further comprising displacing a rack and pinion mechanism.

11. The method of claim 8, wherein actuating the steering member comprising actuating with steering member with only one hand.

12. The method of claim 8, wherein the steering member includes:
a gear secured in a position within the longitudinal passage and configured to mesh with the first and second racks;
the button coupled to the first rack and configured to displace the first rack proximally and distally; and
a biasing member disposed between the button and the first rack that actively locks the button into a locked configuration, wherein depressing the button and sliding the button proximally or distally transitions the button to an unlocked configuration.

13. The method of claim 12, wherein:

the first rack includes a first slot extending longitudinally along at least a portion of the first rack, the first wire being looped through the first slot effective to couple the first wire to the first rack; and the second rack includes a second slot extending longitudinally along at least a portion of the second rack, the second wire being looped through the second slot effective to couple the second wire to the second rack.

14. The method of claim 12, further comprising two opposing openings on the tube between the tension control member and the distal end of the tube, wherein the first wire and the second wire extend from the tension control member, at least partially into the tube, to the distal end of the tube.

\* \* \* \* \*